(12) United States Patent
Boudreaux

(10) Patent No.: US 10,245,095 B2
(45) Date of Patent: Apr. 2, 2019

(54) ELECTROSURGICAL INSTRUMENT WITH ROTATION AND ARTICULATION MECHANISMS

(71) Applicant: Ethicon Endo-Surgery, Inc., Cincinnati, OH (US)

(72) Inventor: Chad P. Boudreaux, Cincinnati, OH (US)

(73) Assignee: Ethicon LLC, Guaynabo, PR (US)

( * ) Notice: Subject to any disclaimer, the term of this patent is extended or adjusted under 35 U.S.C. 154(b) by 709 days.

(21) Appl. No.: 14/616,267

(22) Filed: Feb. 6, 2015

(65) Prior Publication Data
US 2016/0228171 A1 Aug. 11, 2016

(51) Int. Cl.
*A61B 18/14* (2006.01)
*A61B 18/00* (2006.01)

(52) U.S. Cl.
CPC .......... *A61B 18/00* (2013.01); *A61B 18/1445* (2013.01); *A61B 2018/0063* (2013.01); *A61B 2018/00184* (2013.01); *A61B 2018/00196* (2013.01); *A61B 2018/00202* (2013.01); *A61B 2018/00607* (2013.01); *A61B 2018/1455* (2013.01)

(58) Field of Classification Search
CPC . A61B 18/1442; A61B 18/1445; A61B 17/28; A61B 17/2804
See application file for complete search history.

(56) References Cited

U.S. PATENT DOCUMENTS

| | | | |
|---|---|---|---|
| 2009/0082766 A1* | 3/2009 | Unger | A61B 18/1445 606/51 |
| 2009/0209960 A1* | 8/2009 | Chojin | A61B 18/1445 606/51 |
| 2013/0023868 A1* | 1/2013 | Worrell | A61B 17/07207 606/33 |
| 2013/0274722 A1* | 10/2013 | Kostrzewski | A61B 17/00234 606/1 |
| 2013/0345765 A1* | 12/2013 | Brockman | A61B 17/8855 606/86 R |

* cited by examiner

*Primary Examiner* — Ronald Hupczey, Jr.
*Assistant Examiner* — Bo Ouyang

(57) ABSTRACT

An electrosurgical instrument includes an end effector comprising two movable jaws for grasping tissue therebetween. The jaws connect to an electrosurgical energy source to deliver energy through tissue between the jaws to effect a seal. The jaws include a knife channel to reciprocate a knife therealong for severing tissue held between the jaws. A two-stage articulation joint is coupled to the end effector and to articulation bands configured to articulate the end effector. The two-stage articulation joint includes an outer cut metal tube comprising a plurality of sections and a solid but flexible inner core positioned within the outer cut metal tube. The electrosurgical instrument also may include a rotatable closure ring and a closure link operatively coupled to the rotatable closure ring, a rotatable coupling joint coupled to the articulation section, and/or a hollow flexible tube coupled to the knife and an active rod extending longitudinally therethrough.

21 Claims, 19 Drawing Sheets

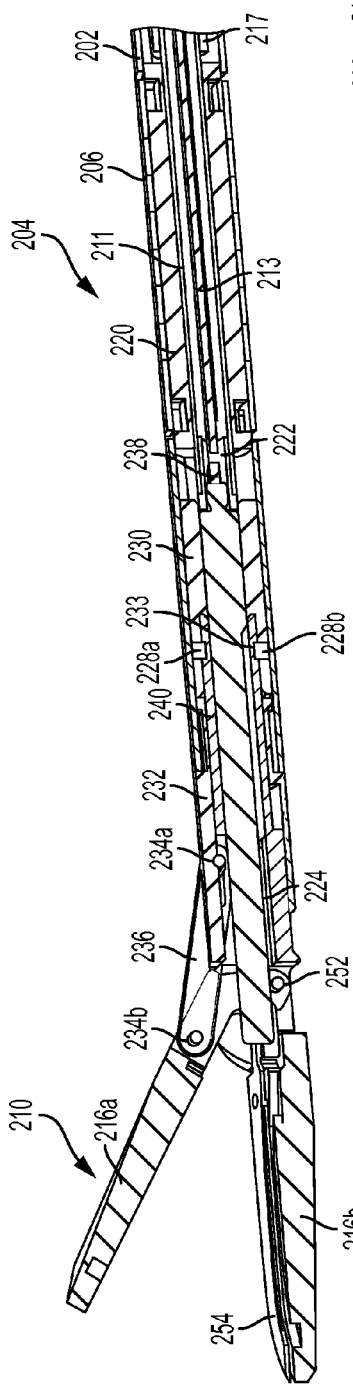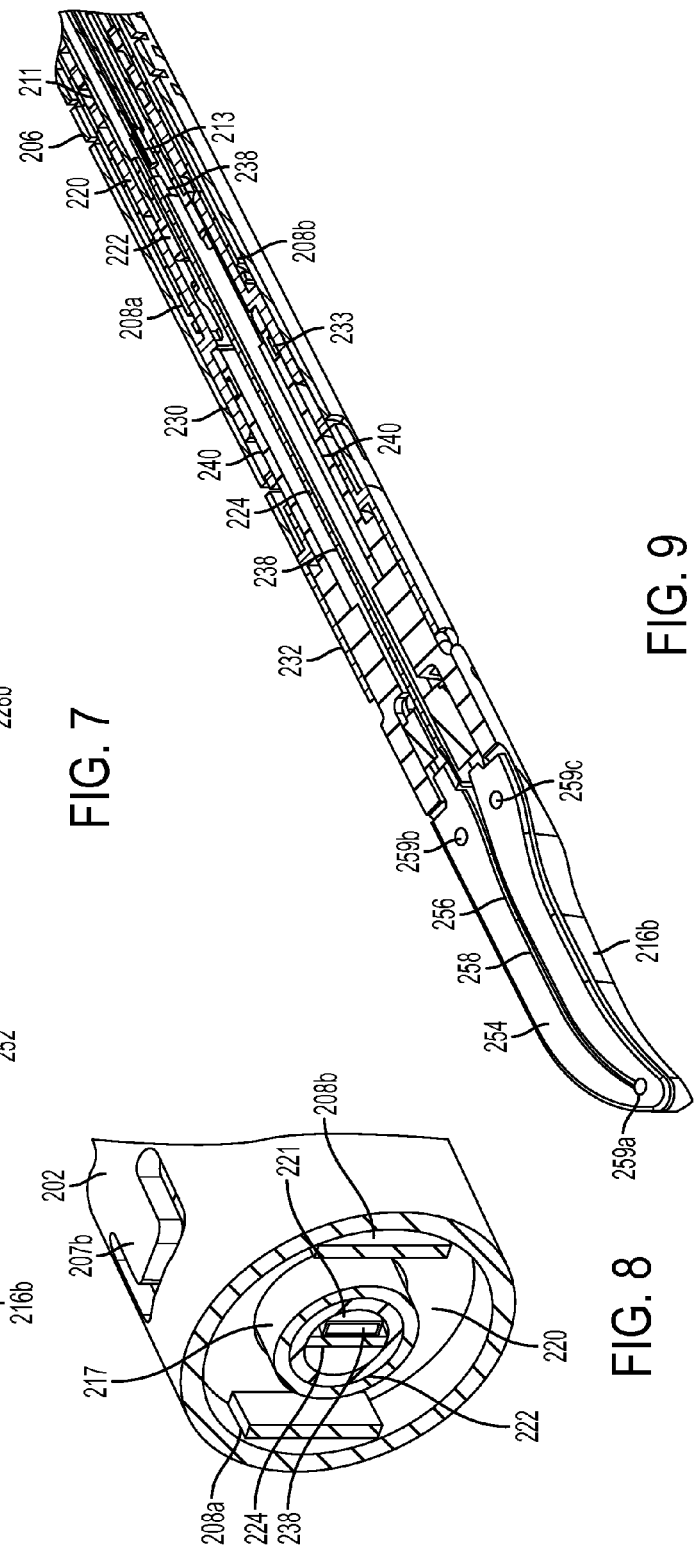

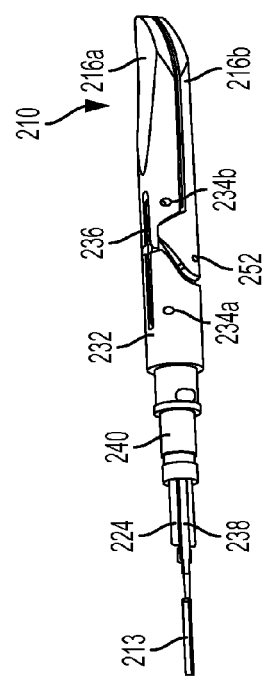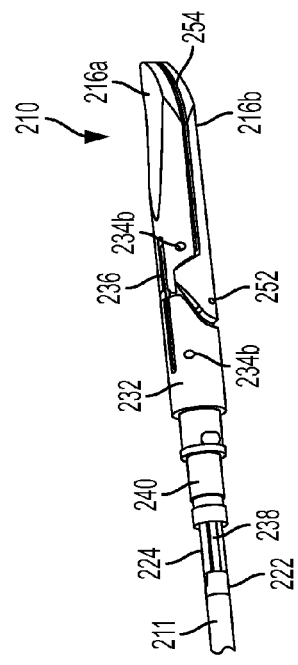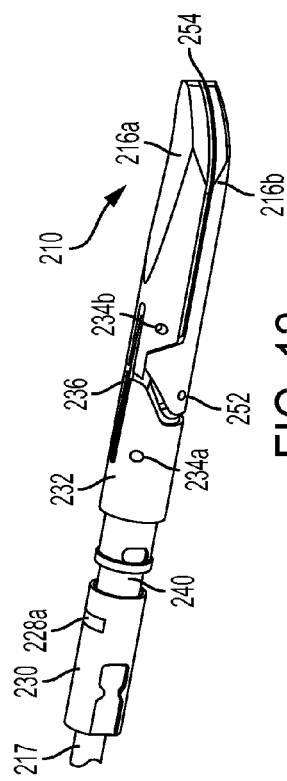

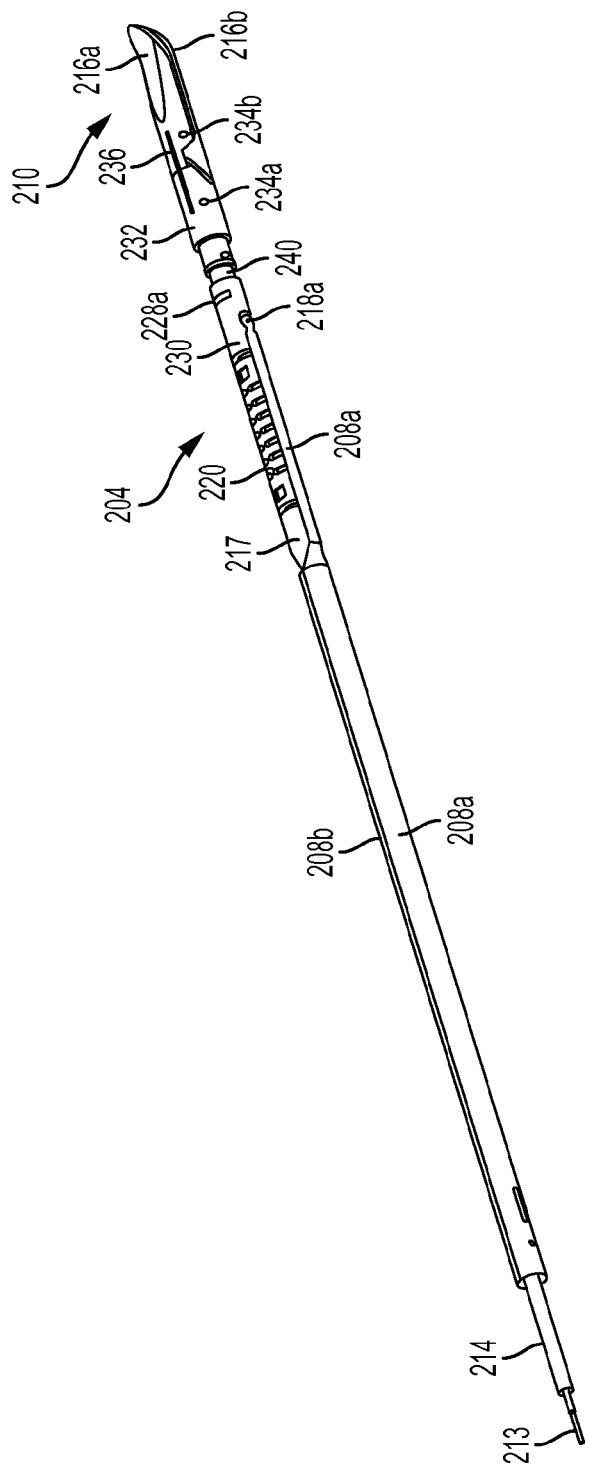
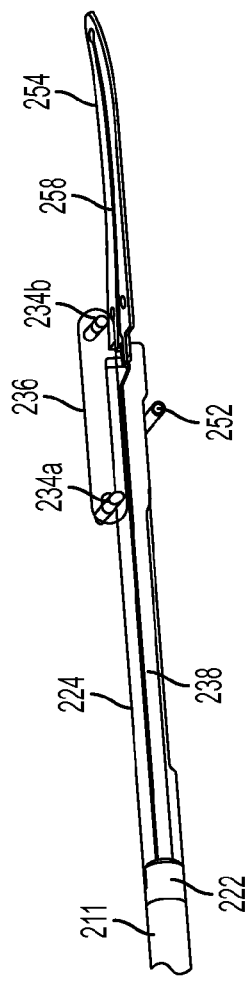
FIG. 13
FIG. 14

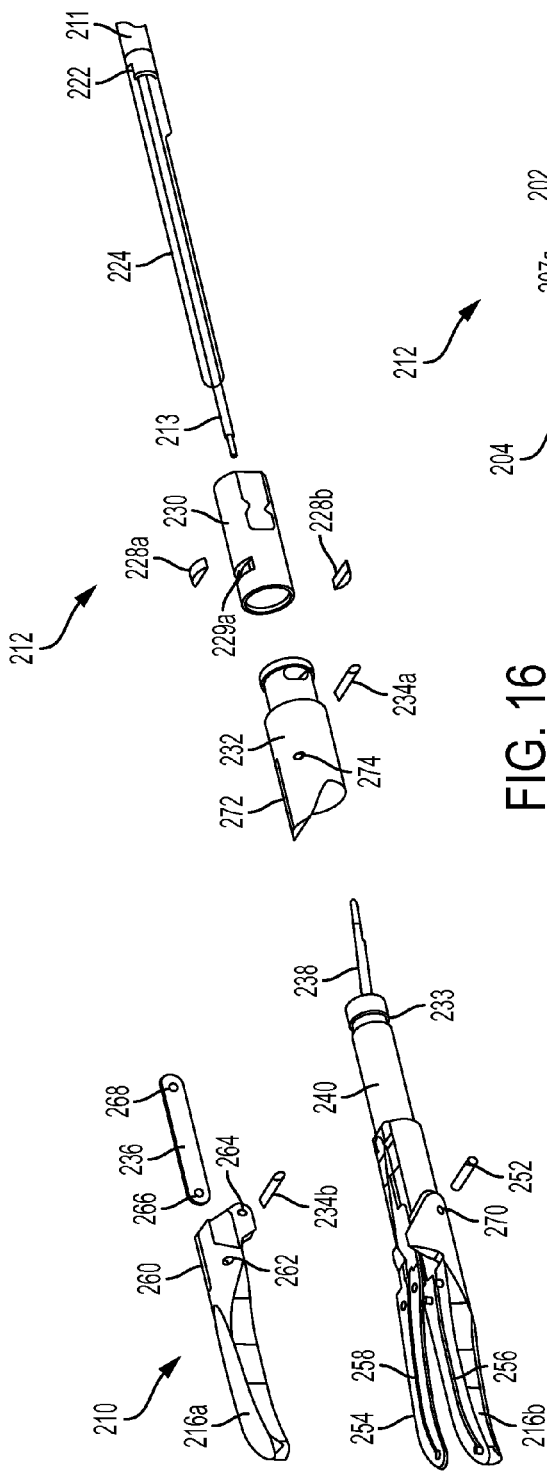
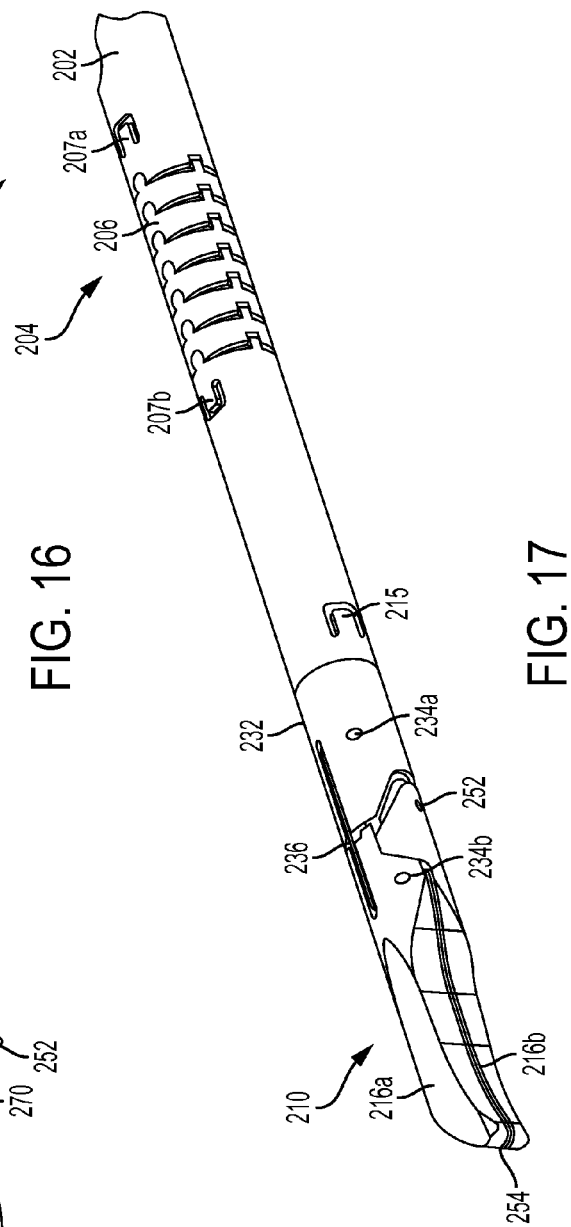
FIG. 16
FIG. 17

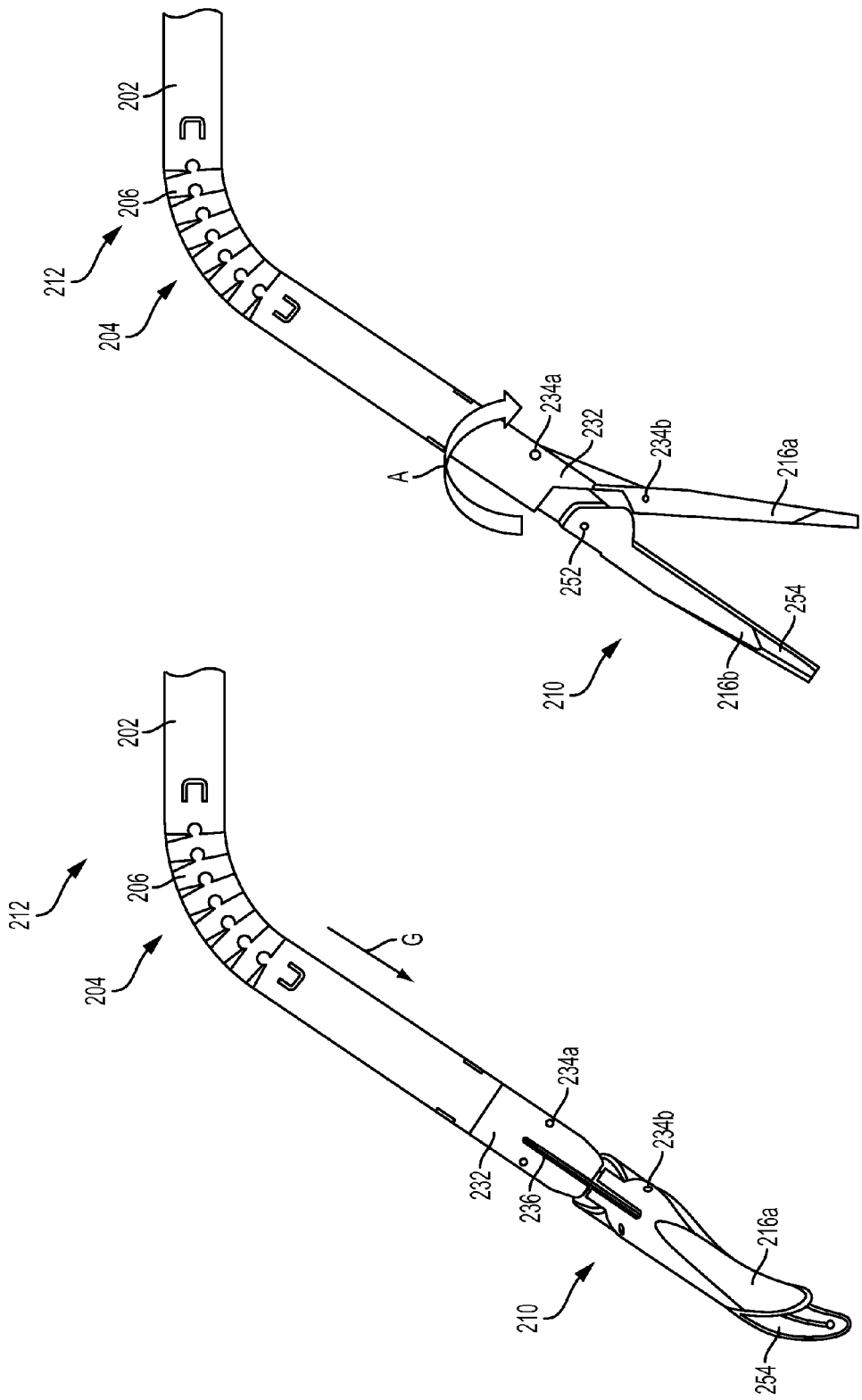

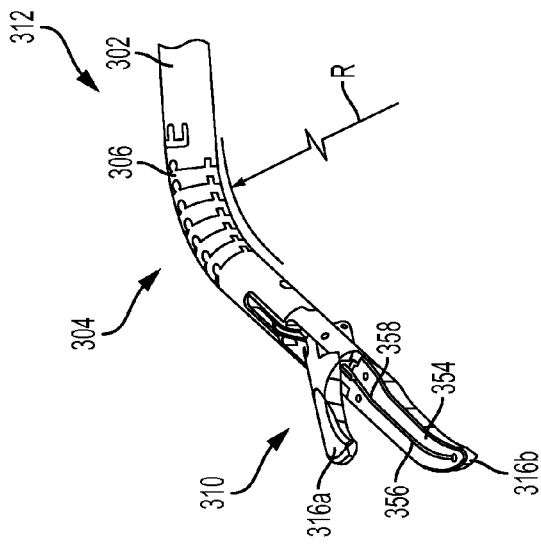
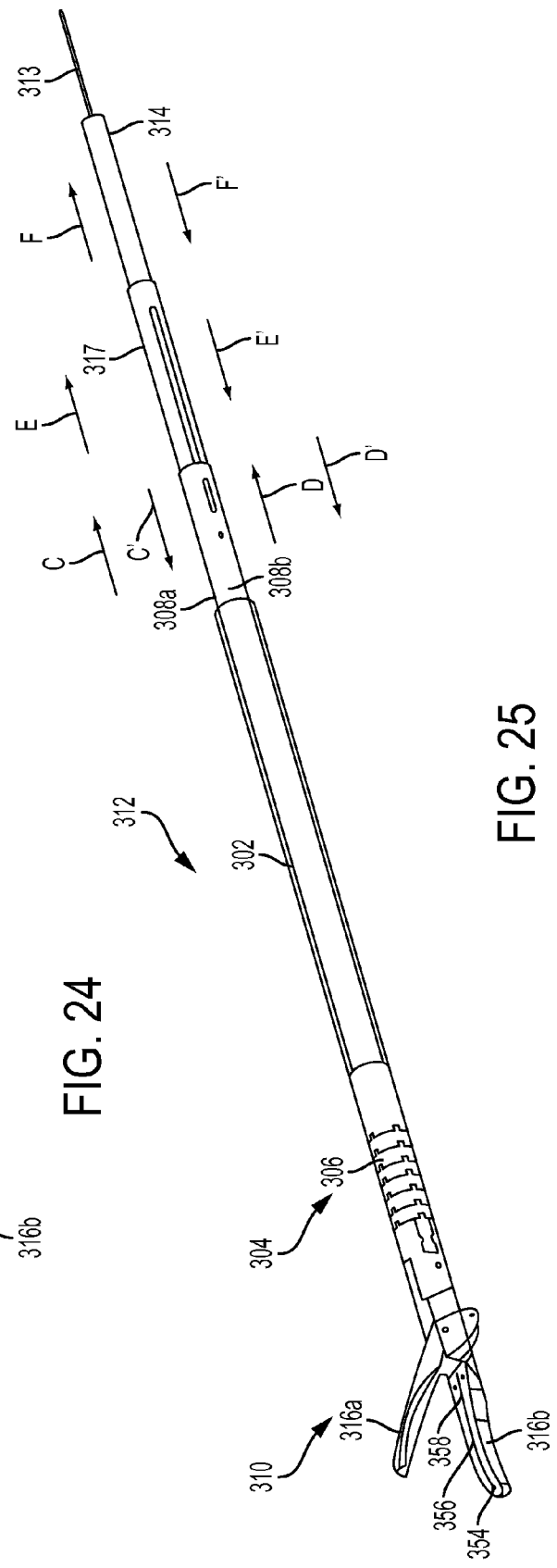
FIG. 24
FIG. 25

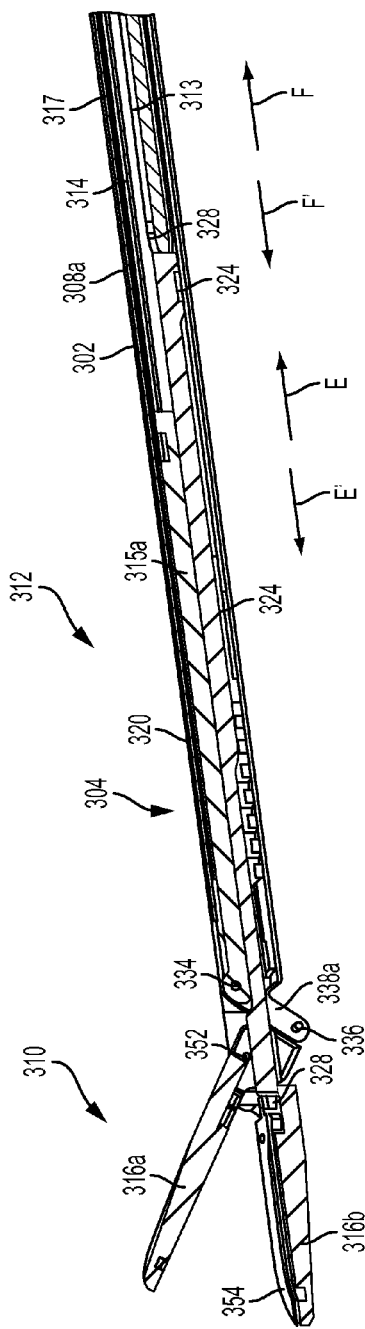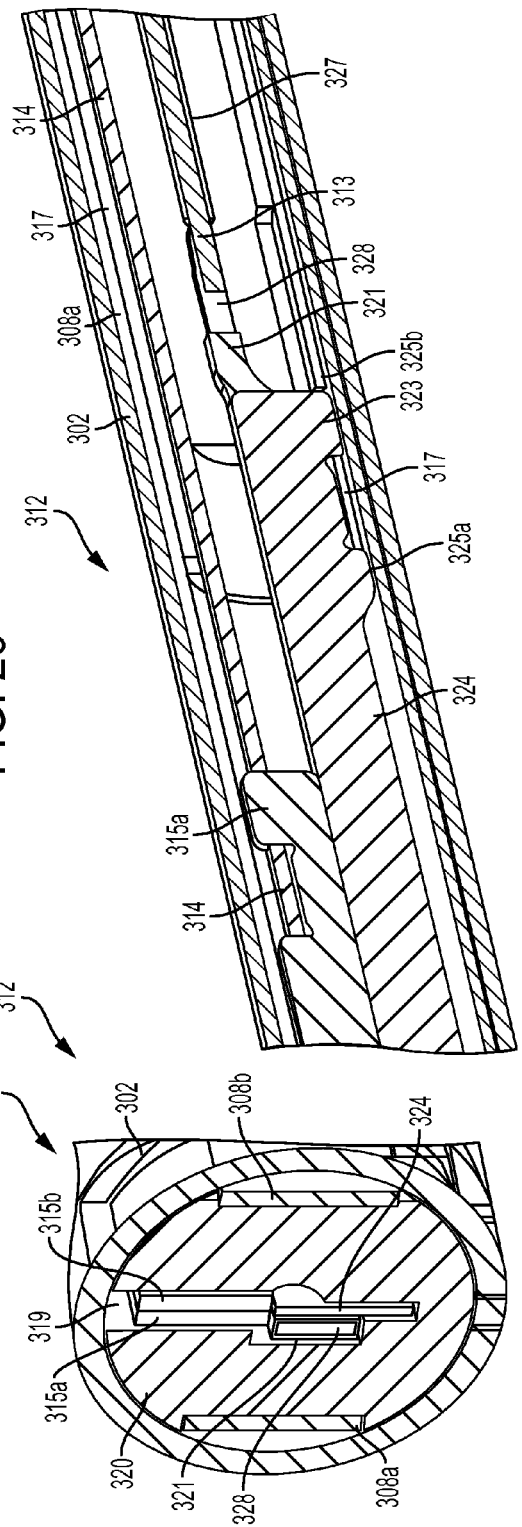

ELECTROSURGICAL INSTRUMENT WITH ROTATION AND ARTICULATION MECHANISMS

INTRODUCTION

The present disclosure is related generally to electrosurgical devices with various mechanisms for clamping and treating tissue. In particular, the present disclosure is related to an electrosurgical device with jaw opening and closing mechanisms. More particularly, the present disclosure is related to an electrosurgical device with jaw opening and closing mechanisms and an articulating shaft.

While several devices have been made and used, it is believed that no one prior to the inventors has made or used the device described in the appended claims.

SUMMARY

In one embodiment, an electrosurgical instrument is disclosed that comprises an end effector comprising a first jaw member and a second jaw member, the first and second jaw members being movable relative to one another from a first, open position to a second, closed position for grasping tissue therebetween, wherein at least one of the jaw members is adapted to connect to an electrosurgical energy source such that electrosurgical energy may be selectively communicated through tissue held between the jaw members to effect a tissue seal; at least one of the first or second jaw members including a knife channel defined therein configured to reciprocate a knife therealong for severing tissue held between the first and second jaw members; and a two-stage articulation joint coupled to the end effector, the two-stage articulation joint operatively coupled to first and second articulation bands configured to articulate the end effector, the two-stage articulation joint comprises an outer cut metal tube comprising a plurality of articulation sections with hinge and locking features that closes and opens the first and second jaw members; and a solid but flexible inner core positioned within the outer cut metal tube.

The electrosurgical instrument may further comprise a two-stage rotatable coupling joint.

The articulation bands of the electrosurgical instrument may be operatively coupled to at least one of the first or second jaw members through the two-stage rotatable coupling joint.

The two-stage rotatable coupling joint of the electrosurgical instrument may comprise a rotatable closure ring and a closure link coupled to the rotatable closure ring, and the outer tube may be attached to the rotatable closure ring.

The link of the electrosurgical instrument may be configured to pull the at least one of the first or second jaw members open relative to the other jaw member and the rotatable closure ring is configured to push the at least one of the first or second jaw members closed relative to the other jaw member.

The end effector of the electrosurgical instrument may be configured to simultaneously rotate and articulate.

The end effector of the electrosurgical instrument may be configured to rotate when the end effector is in an articulated position.

The electrosurgical instrument may further comprise a knife configured to reciprocate within the knife channel and rotate when the end effector is rotated.

The electrosurgical instrument may further comprise a flexible hollow cable and a knife tube, wherein the flexible hollow cable is coupled between the knife and the knife tube such that the knife can be pushed through the articulation section and wherein the flexible hollow cable is located over an electrical conductor.

The electrosurgical instrument may further comprise a rotatable pivot, wherein the articulation bands are coupled to at least one of the first or second jaw members through the rotatable pivot.

In another embodiment, an electrosurgical instrument is disclosed that comprises an end effector comprising a first jaw member and a second jaw member, the first and second jaw members being movable relative to one another from a first, open position to a second, closed position for grasping tissue therebetween, wherein at least one of the jaw members is adapted to connect to an electrosurgical energy source such that electrosurgical energy may be selectively communicated through tissue held between the jaw members to effect a tissue seal; at least one of the first or second jaw members including a knife channel defined therein configured to reciprocate a knife therealong for severing tissue held between the first and second jaw members; a rotatable closure ring; and a closure link operatively coupled to the rotatable closure ring, wherein the rotatable closure ring and the link are configured to rotate the end effector.

The rotatable closure ring of the electrosurgical instrument may be configured to transmit a closure force to the first and second jaw members while the first and second jaw members are rotated relative to the outer tube at any angle.

The electrosurgical instrument may further comprise a knife configured to reciprocate within the knife channel and rotate when the end effector is rotated.

The knife of the electrosurgical instrument may be connected to a knife tube located within the outer tube.

The electrosurgical instrument may further comprise an outer tube comprising an articulation section coupled to the end effector, the articulation section operatively coupled to first and second articulation bands configured to articulate the end effector.

In another embodiment, an electrosurgical instrument is disclosed that comprises an end effector comprising a first jaw member and a second jaw member, the first and second jaw members being movable relative to one another from a first, open position to a second, closed position for grasping tissue therebetween; at least one of the first or second jaw members including a knife channel defined therein configured to reciprocate a knife therealong for severing tissue held between the first and second jaw members; at least one articulation band; an articulation section coupled to the end effector, the articulation section operatively coupled to the at least one articulation band configured to articulate the end effector; and a rotatable coupling joint coupled to the articulation section.

The electrosurgical instrument may further comprise at least a second articulation band, wherein the first and second articulation bands are coupled to the rotatable coupling joint.

The electrosurgical instrument may further comprise a closure tube and a handle assembly operably coupled to the end effector, wherein the first jaw member is movable with respect to the second jaw member, and wherein the first jaw member is coupled to the closure tube and the second jaw member is coupled to the hand assembly.

The at least one articulation band of the electrosurgical instrument may be coupled to the second jaw member through the rotatable coupling joint.

In another embodiment, an electrosurgical instrument is disclosed that comprises an end effector comprising a first jaw member and a second jaw member, the first and second jaw members being movable relative to one another from a first, open position to a second, closed position for grasping tissue therebetween; a knife; at least one of the first and second jaw members including a knife channel defined therein configured to reciprocate the knife therealong for severing tissue held between the jaw members; an outer tube coupled to the end effector; a rotatable coupling joint coupled to the end effector; a hollow flexible tube coupled to the knife, the hollow flexible tube defining a space therein; and an active rod that extends longitudinally within the hollow space defined by the hollow flexible tube.

The hollow flexible tube of the electrosurgical instrument may be rotatably coupled to the end effector and is configured to rotate the end effector through the knife.

The active rod of the electrosurgical instrument may be configured to electrically couple to one electrical pole of an energy source.

The electrosurgical instrument may further comprise at least one jaw electrode electrically coupled to at least one of the first or second jaw members, wherein the at least one jaw electrode is adapted to connect to an electrosurgical energy source such that electrosurgical energy may be selectively communicated through tissue held between the first and second jaw members to effect a tissue seal, wherein the at least one jaw electrode defines at least one aperture.

The electrosurgical instrument may further comprise at least one stop member located on at least one of the first or second jaw members, wherein the stop member in configured to protrude through the at least one aperture of the at least one jaw electrode and to control a gap distance between the first and second jaw members.

The foregoing summary is illustrative only and is not intended to be in any way limiting. In addition to the illustrative aspects, embodiments, and features described above, further aspects, embodiments, and features will become apparent by reference to the drawings and the following detailed description.

FIGURES

The novel features of the embodiments described herein are set forth with particularity in the appended claims. The embodiments, however, both as to organization and methods of operation may be better understood by reference to the following description, taken in conjunction with the accompanying drawings as follows:

FIG. 7 is a sectional view of the articulation section of the shaft assembly and end effector of the surgical instrument shown in FIGS. 1-3, according to one embodiment.

FIG. 8 is sectional view of the outer tube, according to one embodiment.

FIG. 9 is a sectional view of the outer tube and the second jaw member, according to one embodiment.

FIG. 10 is a perspective view of the end effector portion of the surgical instrument shown in FIGS. 1-3 with the active rod installed, according to one embodiment.

FIG. 11 is a perspective view of the end effector portion of the surgical instrument shown in FIG. 10 with the adapter and the hollow flexible knife cable installed, according to one embodiment.

FIG. 12 is a perspective view of the end effector portion of the surgical instrument shown in FIG. 11 with the anchor installed over the neck of the second jaw member, according to one embodiment.

FIG. 13 is a perspective view of the end effector portion of the surgical instrument shown in FIG. 12 with the flexible neck, knife tube, articulation bands, and spacer tube installed, according to one embodiment.

FIG. 14 is a detail view of the electrode relative to the link, according to one embodiment.

FIG. 16 is a partial exploded view showing the assembly of the end effector and the shaft assembly of the surgical instrument shown in FIGS. 1-3, according to one embodiment.

FIG. 17 is a final assembly of the end effector and the shaft assembly of the surgical instrument shown in FIGS. 1-3, according to one embodiment.

FIG. 18 is a view of the end effector and shaft assembly of the surgical instrument shown in FIGS. 1-3 in an articulated position and the jaws in an open position, according to one embodiment.

FIG. 19 is a view of the end effector and shaft assembly of the surgical instrument shown in FIGS. 1-3 in an articulated position and the jaws in an open position, according to one embodiment.

FIG. 24 is a perspective view of a shaft assembly in an articulated position and an end effector with jaw members in an open position, according to one embodiment.

FIG. 25 is a perspective view of the shaft assembly and end effector shown in FIG. 24 in an unarticulated (straight) position with the jaw members in a closed position, according to one embodiment.

FIG. 26 is a sectional view of the shaft assembly and end effector, according to one embodiment.

FIG. 27 is a sectional view of the shaft assembly and end effector, according to one embodiment.

FIG. 28 is a longitudinal sectional view of the shaft assembly, according to one embodiment.

DESCRIPTION

Figure 1:
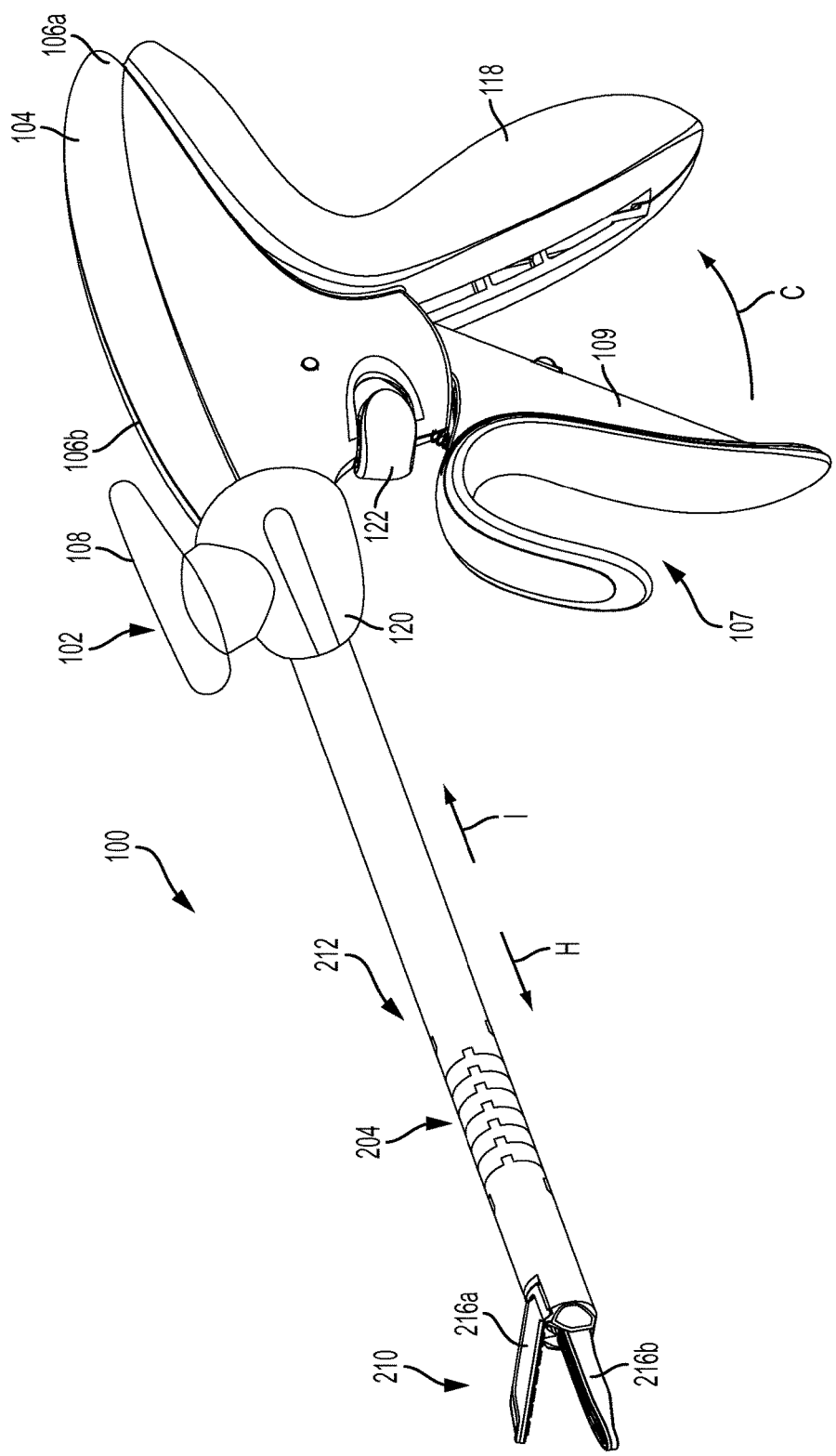
FIG. 1 illustrates a surgical instrument comprising an articulating shaft mechanism, according to one embodiment.

In the following detailed description, reference is made to the accompanying drawings, which form a part hereof. In the drawings, similar symbols and reference characters typically identify similar components throughout the several views, unless context dictates otherwise. The illustrative embodiments described in the detailed description, drawings, and claims are not meant to be limiting. Other embodiments may be utilized, and other changes may be made, without departing from the scope of the subject matter presented here.

The following description of certain examples of the technology should not be used to limit its scope. Other examples, features, aspects, embodiments, and advantages of the technology will become apparent to those skilled in the art from the following description, which is by way of illustration, one of the best modes contemplated for carrying out the technology. As will be realized, the technology described herein is capable of other different and obvious aspects, all without departing from the technology. Accordingly, the drawings and descriptions should be regarded as illustrative in nature and not restrictive.

It is further understood that any one or more of the teachings, expressions, embodiments, examples, etc. described herein may be combined with any one or more of the other teachings, expressions, embodiments, examples, etc. that are described herein. The following-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Before explaining the various embodiments of the surgical devices having an articulating shaft mechanism in detail, it should be noted that the various embodiments disclosed herein are not limited in their application or use to the details of construction and arrangement of parts illustrated in the accompanying drawings and description. Rather, the disclosed embodiments may be positioned or incorporated in other embodiments, variations and modifications thereof, and may be practiced or carried out in various ways. Accordingly, embodiments of the surgical devices disclosed herein are illustrative in nature and are not meant to limit the scope or application thereof. Furthermore, unless otherwise indicated, the terms and expressions employed herein have been chosen for the purpose of describing the embodiments for the convenience of the reader and are not to limit the scope thereof. In addition, it should be understood that any one or more of the disclosed embodiments, expressions of embodiments, and/or examples thereof, can be combined with any one or more of the other disclosed embodiments, expressions of embodiments, and/or examples thereof, without limitation.

Also, in the following description, it is to be understood that terms such as front, back, inside, outside, top, bottom and the like are words of convenience and are not to be construed as limiting terms. Terminology used herein is not meant to be limiting insofar as devices described herein, or portions thereof, may be attached or utilized in other orientations. The various embodiments will be described in more detail with reference to the drawings.

Turning now to the figures, where FIG. 1 illustrates a surgical instrument 100 comprising a trigger assembly 107, a shaft assembly 212, and articulation joint 204, and an end effector 210. An articulation control knob 102 controls the articulation of the articulation joint 204 by way of articulation cables or bands operably coupled to the articulation control knob 102. A rotation knob 120 is operably coupled to the shaft assembly 212 and enables rotation of the shaft assembly 212 up to and including 360 degrees. The trigger assembly 107 is configured to clamp and independently fire the end effector 210 coupled to the shaft assembly 212 of the surgical instrument 100. In the embodiment shown in FIG. 1, the first jaw member 216a of the end effector 210 is fully open and the articulation control knob 108 is in a neutral, central, position.

The surgical instrument 100 comprises a handle assembly 104. The shaft assembly 212 comprises a proximal end and a distal end. The proximal end of the shaft assembly 212 is coupled to the distal end of the handle assembly 104. The articulation control knob 108 and the rotation control knob 120 are operatively coupled to the distal end of the handle assembly 104 and are configured to receive and couple to the proximal end of shaft assembly 212. The end effector 210 is coupled to the distal end of the shaft assembly 212. The handle assembly 104 comprises a pistol grip 118. The handle assembly 104 comprises a left handle housing shroud 106a and a right handle housing shroud 106b. The trigger assembly 107 comprises a trigger 109 actuatable towards the pistol grip 118. The rotatable shaft knob 120 is configured to rotate the shaft assembly 212 with respect to the handle assembly 104. The handle assembly 104 further comprises an energy button 122 configured to provide electrosurgical energy to one or more electrodes in the end effector 210.

The shaft assembly 212 comprises a closure/jaw actuator, a firing/cutting member actuator, and an outer sheath. In some embodiments, the outer sheath comprises the closure actuator. The outer sheath comprises one or more contact electrodes on a distal end configured to interface with the end effector 210. The one or more contact electrodes are operatively coupled to the energy button 122 and an energy source (not shown).

The energy source may be suitable for therapeutic tissue treatment, tissue cauterization/sealing, as well as sub-therapeutic treatment and measurement energy source. The energy button 122 controls the delivery of energy to the electrodes. As used throughout this disclosure, a button refers to a switch mechanism for controlling some aspect of a machine or a process. The buttons may be made out of a hard material such as usually plastic or metal. The surface may be formed or shaped to accommodate the human finger or hand, so as to be easily depressed or pushed. Buttons can be most often biased switches, even though many un-biased buttons (due to their physical nature) require a spring to return to their un-pushed state. Terms for the "pushing" of the button, may include press, depress, mash, and punch.

In some embodiments, an end effector 210 is coupled to the distal end of the shaft assembly 212. The end effector 210 comprises a first jaw member 216a and a second jaw member 216b. The first jaw member 216a is pivotally coupled to the second jaw member 216b. The first jaw member 216a is pivotally moveable with respect to the second jaw member 216b to grasp tissue therebetween. The first jaw member 216a may be referred to as the upper jaw or upper jaw member. In some embodiments, the second jaw member 216b is fixed. The second jaw member 216b may be referred to as the lower jaw or lower jaw member. In other embodiments, the first jaw member 216a and the second jaw member 216b are pivotally movable. In one example, at least one of the jaw members 216a, 216 is fixed relative to the shaft 212 assembly. In another example both jaw members 216a, 216b are movable relative to the shaft assembly 212. In the illustrated example, the first jaw member 216a is movable relative to shaft assembly 212 and the second jaw member 216b is fixed relative to the shaft assembly 212. The jaw members 216a, 216b are movable relative to one another from a first, open position to a second, closed position for grasping tissue therebetween.

At least one of the jaw members 216a, 216b is adapted to connect to an electrosurgical energy source such that electrosurgical energy may be selectively communicated through tissue held between the jaw members 216a, 216b to effect a tissue seal. At least one of the jaw members 216a, 216b of the end effector 210 comprises at least one electrode 254 adapted to connect to an electrosurgical energy source and configured to deliver energy to tissue held between the jaw members 216a, 216b to effect a tissue a seal. The electrosurgical energy source may comprise, for example, a radiofrequency (RF) energy source, a sub-therapeutic RF energy source, an ultrasonic energy source, and/or other suitable energy source. Where multiple energy sources are used, the energy may be delivered either independently or in combination. In some embodiments, a cutting member (not shown) is receivable within a longitudinal slot defined by the first jaw member 216a and/or the second jaw member 216b. The cutting member is configured to cut tissue grasped between the first jaw member 216a and the second jaw member 216b. In some embodiments, the cutting member comprises an electrode for delivering energy, such as, for example, RF, ultrasonic energy, or a combination thereof that can be delivered independently or in combination.

In certain instances, as described above, the surgical instrument 100 may include an automatic energy lockout mechanism. The energy lockout mechanism can be associated with a closure mechanism of the surgical instrument 100. In certain instances, the energy lockout mechanism can be configured to permit energy delivery to the end effector 210 when the energy delivery button 122 is actuated if the jaw members 216a, 216b are in an open configuration. In certain instances, an energy lockout mechanism may be configured to deny energy delivery to the end effector 210 when the energy delivery button 122 is actuated if the jaw members 216a, 216b are in a closed configuration. In certain instances, the energy lockout mechanism automatically transitions from permitting the energy delivery to denying the energy delivery when the jaw members 216a, 216b are transitioned from the closed configuration to the open configuration, for example. In certain instances, the energy lockout mechanism automatically transitions from denying the energy delivery to permitting the energy delivery when the jaw members 216a, 216b are transitioned from the open configuration to the closed configuration, for example.

Figure 2:
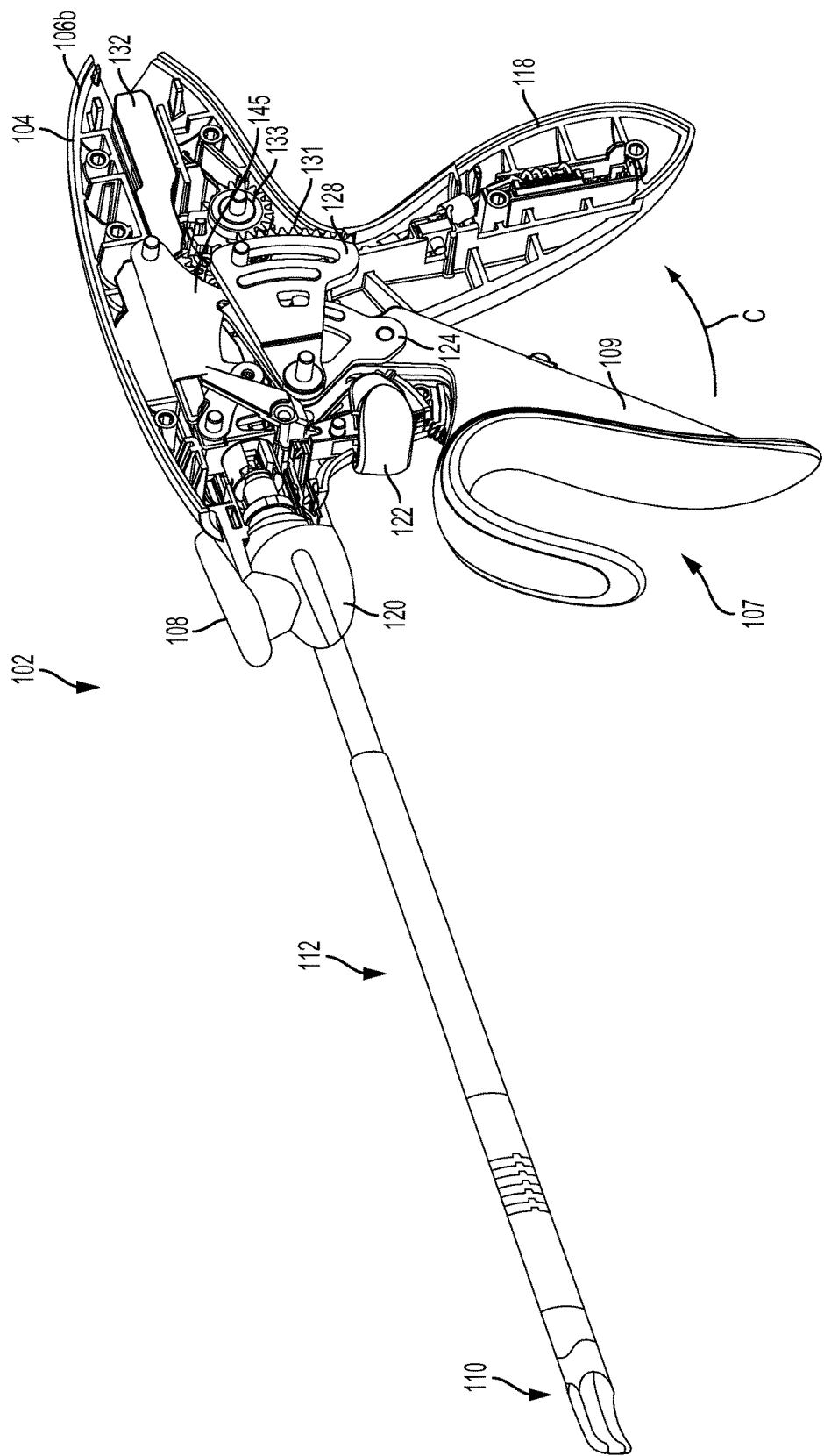
FIG. 2 is a perspective view of a handle assembly of the surgical instrument illustrated in FIG. 1 with the left handle housing shroud and several sheaths in the shaft assembly removed, according to one embodiment.

FIG. 2 is a perspective view of a handle assembly 104 of a surgical instrument 100 illustrated in FIG. 1, according to one embodiment, with the right housing shroud 106a removed to show some of the internal mechanisms. The trigger assembly 107 comprises the necessary components for closing the jaw members 216a, 216b and firing the cutting member or knife bands. The trigger assembly 107 comprises a trigger plate 124 and firing plate 128 operatively coupled to the trigger 109. Squeezing the trigger 109 in direction C towards the pistol grip 118 rotates the trigger plate 124 which operates the toggle clamp 145 to advance a yoke 132 and a closure actuator 123 distally to close the jaw members 216a, 216b of the end effector 210. Initial rotation of the trigger plate 124 also slightly rotates the firing plate 128. The firing plate 128 comprises a sector gear with a plurality of teeth 131 that engage and rotate a first pinion gear 133, which engages a second pinion gear 134 to advance a rack 136 (neither is shown in this view).

The single trigger 109 closes the jaws in the first ~13 degrees of stroke. The trigger plate 124 is configured to interface with the trigger plate 124 during rotation of the trigger 109 from an initial position to a first rotation, which is ~13 degrees of stroke, for example. The trigger plate 124 is operably coupled to the firing plate 128. In certain instances, the firing plate 128 may include a first slot 128a and a second slot 128b. The first slot 128a receives a drive pin 148 fixedly coupled to the trigger plate 124. The pin 148 slidably moves within the first slot 128a. Rotation of the trigger plate 124, while the pin 148 is slidably received within the first slot 128a, drives rotation of the firing plate 128. The teeth 131 of the sector gear engage and rotate the first pinion 133, which in turn drives the second pinion 134, which drives the rack 136 distally to fire the knife, or knife, but only when the knife lockout is unlocked, released, or disabled.

The single trigger 109 fires the knife in the last ~29 degrees of stroke. Rotation of the trigger plate 124 beyond a predetermined rotation such as, for example, the first rotation, causes rotation of the firing plate 128. Rotation of the firing plate 128 deploys a cutting member within the end effector 210. For example, in the illustrated embodiment, the firing plate 128 comprises a sector gear operably coupled to a rack 136 through the first and second pinions 133, 134. The firing plate 128 comprises a plurality of teeth 131 configured to interface with the first pinion 133. Rotation of the firing plate 128 rotates the first and second pinions 133, 134, to drive the rack 136 distally. Distal movement of the rack 136 drives the cutting member actuator distally, causing deployment of the cutting member (e.g., knife) within the end effector 210.

The shaft assembly 212 comprises a closure/jaw actuator and a firing/cutting member actuator. The closure/jaw actuator comprises a yoke 132 and toggle clamp 145 assembly operatively coupled to a closure actuator 212 which acts on a closure spring 114 coupled to a spring-to-bar interface element 127 and a closure bar 116. In one instance the closure bar is operatively coupled to the jaw members 216a, 216b via at least one linkage. The firing/cutting member actuator comprises a rack 136 operatively coupled to a firing bar, which is slidably received within the closure actuator 212 and the closure spring. The firing bar is coupled to a knife pusher block and a flexible knife band comprising multiple flexible bands fastened together and a knife at the distal end. Advancing the rack 136 in the distal direction advances the knife band distally through a channel or slot formed in the jaw members 216a, 216b.

Figure 3:
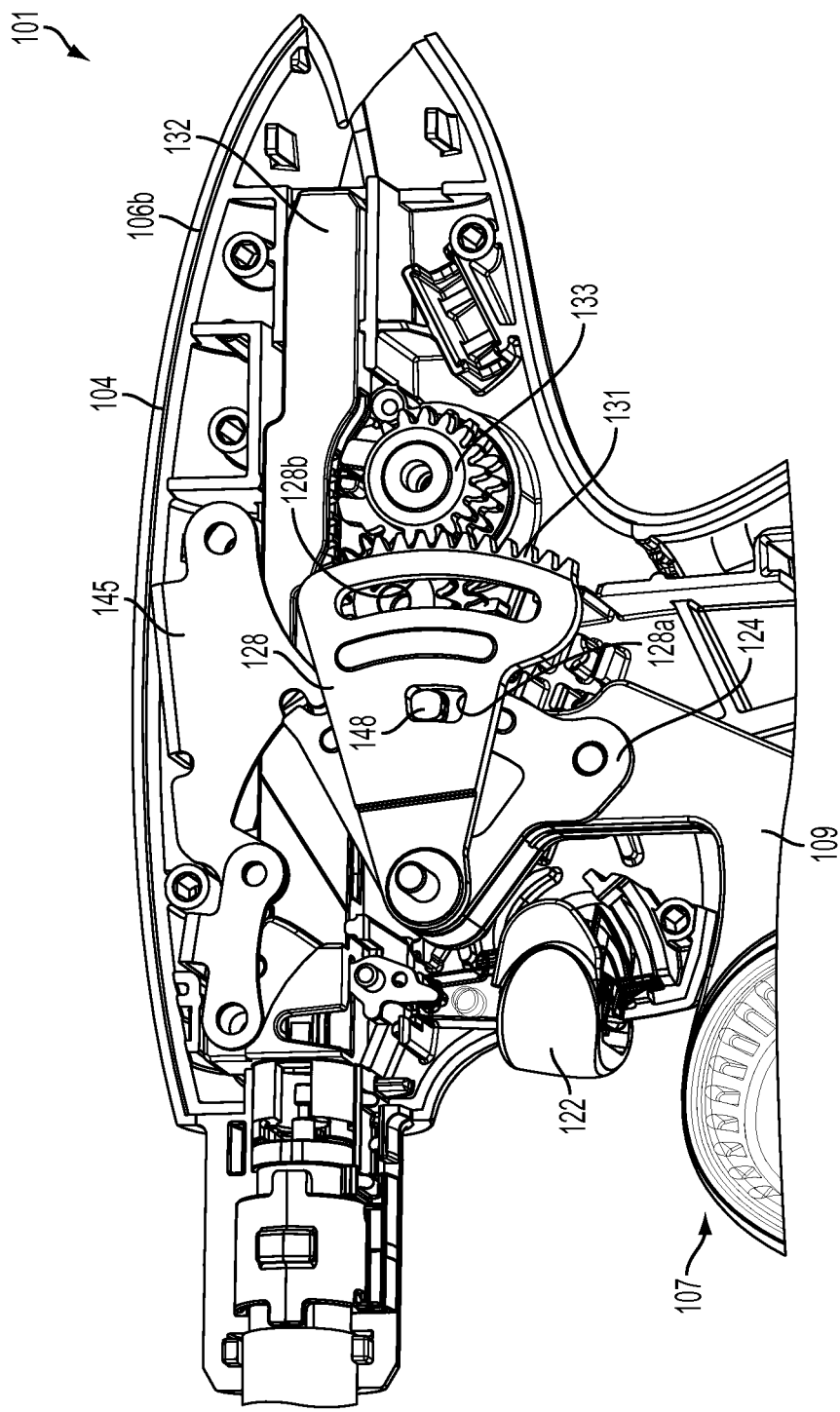
FIG. 3 is a side elevation view of a handle assembly of a surgical instrument, similar to the surgical instrument shown in FIGS. 1 and 2, with the left handle housing shroud removed, and without the lockout disabling mechanism, according to one embodiment.

FIG. 3 is a side elevation view of a handle assembly 104 of a surgical instrument 101, with the left handle housing shroud 106a removed to expose various mechanisms located within the handle assembly 104, according to one embodiment. In other aspects, the surgical instrument 101 operates in a manner similar to the surgical instrument described in connection with FIGS. 1 and 2.

FIGS. 4-23 illustrate various embodiments of electrosurgical instruments comprising an articulating shaft mechanisms. In one embodiment, the electrosurgical instrument comprises a rotatable shaft with an articulation mechanism and an end effector jaw push mechanism. In one embodiment, the electrosurgical instrument comprises an articulating bipolar radio frequency (RF) device with jaws, articulation bands, and a combination of internal flexible guide and external laser cut outer tube to form an articulation joint. In one embodiment, the electrosurgical instrument comprises an end effector configured to rotate when the knife rotates. In one embodiment, the electrosurgical instrument comprises a closure ring and a link. The link pulls the jaws open and the closure ring pushes the jaws shut. In one embodiment, the electrosurgical instrument comprises a flexible hollow cable to join the knife and a tube such that the knife can be rotated and pushed through the joint and such that the cable can ride over one of the RF electrodes provided in the jaws of the end effector. In one embodiment, the electrosurgical instrument comprises articulation bands are provided that attach to one of the jaws through a rotatable pivot. In one embodiment, an outer tube is attached to the closure ring through a rotatable pivot. In various embodiments, the present disclosure provides electrosurgical instruments that comprise a combination of some or all of these features without limitation.

In connection with the embodiments of the electrosurgical instrument described in FIGS. 4-23, the articulation mechanism can provide up to 55 degrees of articulation. Additional or fewer degrees of articulation may be provided by adding or removing joints, as described in more detail hereinbelow. Additional or fewer joints may be provided to reduce or increase the articulation arc of the articulation section. A rotation mechanism enables the jaw to rotate up to and including 360 degrees distal of the articulation section. A closure tube is provided to push the jaw shut to maximize closure mechanical advantage and a link is used to open the jaws to maximize opening mechanical advantage. Employing an outer tube for closing the jaws saves internal space and enables the closure mechanism to be disposed down the center of the shaft to reduce changes to opening and closing strokes when the shaft is in an articulated position. An active rod, used to energize an end effector electrode, and a knife (e.g., knife) cable also are centrally disposed along the length of the shaft, such that they rotate together and eliminate the need for a complex wire path. Assembly of the electrosurgical instrument may be easier than conventional articulating instruments. Embodiments of the electrosurgical instrument comprise a joint to jaw length that is, where the jaw is larger than conventional electrosurgical instruments. Embodiments of the electrosurgical instrument provide improved dissection and grasping and enable the jaws to seal tissue before cutting the tissue.

Figure 4:
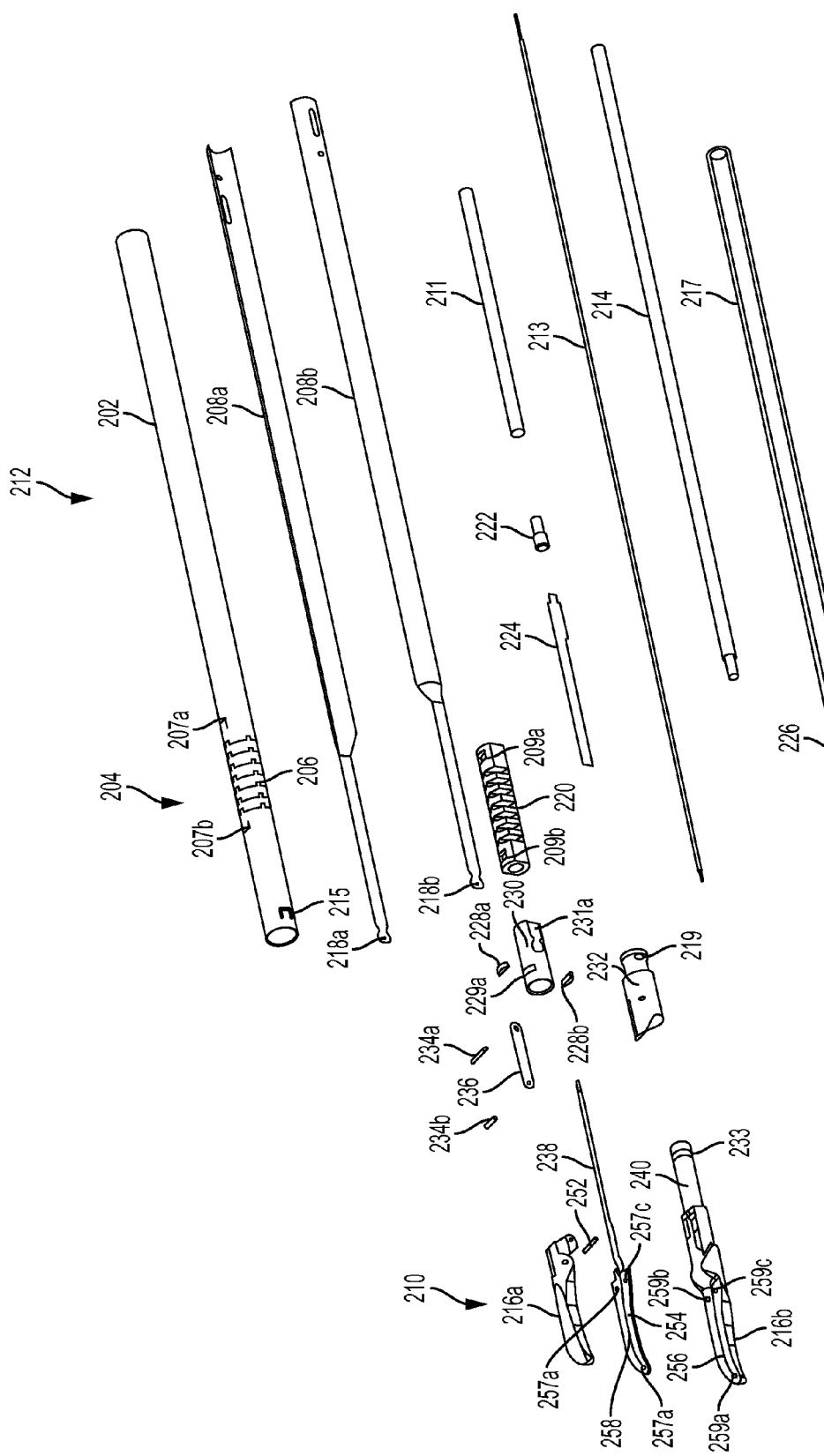
FIG. 4 is an exploded view of the shaft assembly and end effector portions of the surgical instrument shown in FIGS. 1-3, according to one embodiment.

FIG. 4 is an exploded view of the shaft assembly 212 and end effector 210 portions of the surgical instrument 100, 101 shown in FIGS. 1-3, according to one embodiment. In the illustrated embodiment, the shaft assembly 212 comprises an outer tube 202, which may be referred to as a closure tube or jaw tube. The outer tube 202 comprises an articulation section 206 and tabs 207a, 207b to couple the outer tube 202 to a flexible neck 220 at corresponding recesses 209a, 209b. The outer tube 202 also comprises a distal tab 215 to couple the outer tube 202 to a slot 219 formed in the rotatable closure ring 232. Although the outer tube 202 may be coupled to the flexible neck 220 and rotatable closure ring 232 using any suitable technique, in the illustrated embodiment these elements are joined by crimping the two tabs 207a, 207b located near the articulation section 206 to the corresponding recesses 209a, 209b on the flexible neck 209a, 209b and the distal tab to the aperture 219 of the rotatable closure ring 232.

First and second articulation bands 208a, 208b are located inside the closure tube 202 and function to articulate the outer tube 202 at the articulation joint 204. The articulation joint 204 comprises a plurality articulation section 206. Each articulation band 208a, 208b comprises a distal end 218a, 218b that is configured to couple to the sides of a non-rotatable closure ring 230. The non-rotatable closure ring 230 comprises a flat portion 231a on one side and a similar flat portion 231b (not shown) on the opposite side. The distal ends 218a, 218b of the articulation bands 208a, 208b are coupled to the corresponding flat portions 231a, 231b (not shown) of the non-rotatable closure ring 230. Although various techniques may be employed to couple the articulation bands 208a, 208b to the non-rotatable closure ring 230, in the illustrated embodiment, the distal ends 218a, 218b of the articulation bands 208a, 208b are connected to the flat portions 231a, 231b (not shown) on either side of the non-rotatable closure ring 230.

A two-stage articulation joint 204 comprises an outer sectioned or cut (e.g., laser cut or simply cut) metal tube comprising a plurality of articulation sections 206 cut into the outer tube 202 with hinge and locking features that closes and opens the jaw members 216a, 216b and a solid but flexible inner core 220 positioned within the outer cut metal tube. The two stage articulation joint 204 guides the knife 224 and articulation bands 208a, 208b through the articulation joint 204. Having the outer metal articulation sections 206 closing and opening the jaw members 216a, 216b frees up space on the inside for more features such as jaw rotation, among others. The internal solid but flexible inner core 220 joint allows for consistent articulation radius R. The internal solid but flexible inner core 220 can be made of plastic or other solid but flexible materials.

Turning now briefly to the end effector 210 portion of the surgical instrument 100, the end effector 210 comprises a first jaw member 216a and a second jaw member 216b. The first jaw member 216a is pivotally coupled to the second jaw member 216b. The first jaw member 216a can rotatably move between open and closed positions by the outer tube 202 about a pivot pin 252. A link 236 is operatively coupled to the first jaw member 216a and to the outer tube 202 by link pins 234a, 234b. A jaw electrode 254 is located on the second jaw member 216b and is employed to conduct RF energy through tissues clamped between the first and second jaw members 216a, 216b. The jaw electrode 254 is electrically coupled to an electrical conductor 238, which is electrically coupled to an active rod 213. The active rod 213 is electrically coupled to an energy source. The second jaw member 216b comprises a neck 240, which includes a groove 233 at a proximal end thereof. The neck 240 slidably receives the rotatable closure ring 232. Although in the illustrated embodiment, the groove 233 is circumferential, in other embodiments the groove 233 does not need to extend about the diameter of the neck 240. The rotatable closure ring 232 is slidably located over the neck 240 of the second jaw member 216b such the proximal end of the rotatable closure ring 232 is located distally past the circumferential groove 233. A distal end of the non-rotatable closure ring 230 is slidably located over a circumferential ring 233 such that slots 229a, 229b (not shown) formed on the non-rotatable closure ring 230 are aligned with the circumferential groove 233. Once in place, inserts 228a, 228b are located through the slots 229a, 229b (not shown) such that they engage the groove 233. Thus, the non-rotatable closure ring 230 is fixedly coupled to the neck 240 of the second jaw member 216b. Although various techniques may be employed to join the non-rotatable closure ring 230 to the second jaw member 216a, in the illustrated embodiment, the inserts 228a, 228b are connected in place.

In one embodiment, the end effector 210 comprises a two-stage rotatable coupling joint comprising a rotatable closure ring 232 and a closure link 236 combination. A non-rotatable closure ring 230 attaches to the rotatable closure ring 232 and the closure link 236 combination. The rotatable closure ring 232 attaches to the neck 240 of the end effector 210. The combination of the rotatable closure ring 232 and the link 236 can rotate with the end effector 210 jaw members 216a, 216b. Pushing on the rotatable closure ring 232 closes the first jaw member 216a through a camming action (cam tube closure) and pulling on the link 236 opens the first jaw member 216a. The two-stage rotatable closure ring 232 allows the jaw members 216a, 216b closure force to be transmitted to the jaw members 216a, 216b while the jaw members 216a, 216b are rotated relative to the shaft 202 at any angle. Separating the opening and closing mechanisms provides precision closing and opening of the jaw members 216a, 216b. Closing the first jaw member 216a with a cam tube closure mechanism provides good mechanical advantage, while opening the first jaw member 216a with the link 236 provides precise control of the jaw members 216a, 216b (e.g., for dissection). The rotatable closure ring 232 is capable of rotatable relative to the non-rotatable closure ring 230 and forms a rotatable coupling joint. Whereas the longitudinal movement of the rotatable closure ring 232 and the non-rotatable closure ring 230 is synchronized, the closure 232 rotates independently of the non-rotatable closure ring 230.

The articulation bands 208a, 208b are attached to the rotatable coupling joint comprising the rotatable closure ring 232 and the closure link 236. The rotatable coupling joint allows the jaw members 216a, 216b to rotate after the articulation angle is set and still have the jaw member 216a closed no matter what angle the jaw members 216a, 216b are rotated to. The rotatable coupling mechanism disables rotation all of the articulation, knife firing, and jaw closure components through the articulation joint 204, only the active rod 213 and the knife tube 214 rotate. The rotatable coupling joint attached to the articulation bands 208a, 208b allows the second jaw member 216b to be grounded to the handle assembly 104 (FIGS. 1-3) such that the outer closure tube 202 can close the first jaw member 216a onto the second jaw member 206b. In other words the articulation bands 208a, 208b attach to the second jaw member 261b through the rotational coupler.

The first and second jaw members 216a, 216b comprise slots to slidably receive a knife 224 therethrough. At least one of the jaw members 216a, 216b includes a knife channel of slot defined therein configured to reciprocate a knife or cutting member therealong for severing tissue held between the jaw members 216a, 216b. In the illustrated example, the first and second jaw members 216a, 216b comprise a slot 256 to reciprocate the knife 224 therein to sever tissue held between the jaw members 216a, 216b. The jaw electrode 254 also comprises a slot 258 to slidably receive the knife 224. At least one stop member 259a, 259b, 259c is provided to define a predetermined gap between the first and second jaw member 216a, 216b and to electrically isolate the first and second jaw members 216a, 216b to prevent the jaw members 216a, 216b from electrically shorting. The jaw electrode 258 defines apertures 257a, 257b, 257c to receive the stop members 259a, 259b, 259c therethrough.

The proximal end of the knife 224 is fixedly coupled to a distal end of the adapter 222. The proximal end of the adapter 222 is fixedly coupled to a distal end of a hollow flexible knife cable 211. The proximal end of the hollow flexible knife cable 211 is fixedly coupled to a distal end of a knife tube 214. The hollow flexible knife cable 211 is slidably movable within the flexible neck 220, which is located within the articulation joint 204 of the outer tube 202. The distal end of the active rod 213 is electrically coupled to the electrical conductor 238 and the proximal end of the active rod 213 is electrically coupled to an energy source. The active rod 213 is located within the knife tube 214, the hollow flexible knife cable 211, and the adapter 222. The distal end of the active rod 213 is connected to the electrical conductor 238.

The hollow flexible tube 222 is connected to the knife 224 and the active rod 213 that runs through its center. The hollow flexible tube 222 can be rotated to rotate the jaw members 216a, 216b through the knife 224. The active rod 213 travels down the center of the hollow flexible tube 222 for one of the electrical poles of the RF energy path. Positioning the active rod 213 in the center of the shaft 202 enables the active rod 213 to freely rotate and bend in any direction. The active rod 213 and the hollow flexible tube 222 components are configured to rotate and articulate in any direction to enable the jaw members 216a, 261b to rotate and the shaft 202 to articulate.

A spacer tube 217 is located between the articulation bands 208a, 208b and over the knife tube 214. A distal end 226 of the spacer tube 217 is located over the hollow flexible knife cable 211. The spacer tube 217 guides the hollow flexible knife cable 211 and separates the knife tube 214 from the articulation bands 208a, 208b.

Figure 5:
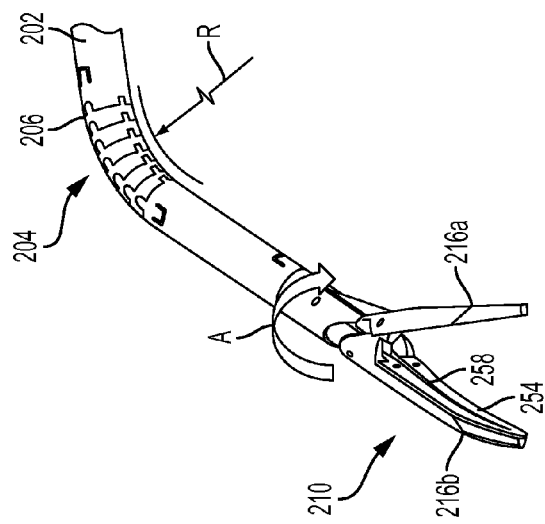
FIG. 5 is a perspective view of the distal end of the outer tube and the end effector of the surgical instrument shown in FIGS. 1-3, according to one embodiment.

FIG. 5 is a perspective view of the distal end of the outer tube 202 and the end effector 210 of the surgical instrument 100, 101 shown in FIGS. 1-3, according to one embodiment. In the illustrated embodiment, the end effector 210 jaw comprising the first and second jaw members 216a, 216b can rotate continuously 360 degrees clockwise, as shown by arrow, or counterclockwise past the articulation joint 204. Although the rotation is shown in the clockwise direction indicated by arrow A, the end effector 210 jaw can be rotated either clockwise or counterclockwise. The end effector 210 jaw can rotate 360 degrees while the articulation joint 204 is in an articulated position. The arc radius of curvature R of the articulation joint 204 can be reduced by adding addition articulation sections 206 and can be increased by removing articulation sections 206.

Figure 6:
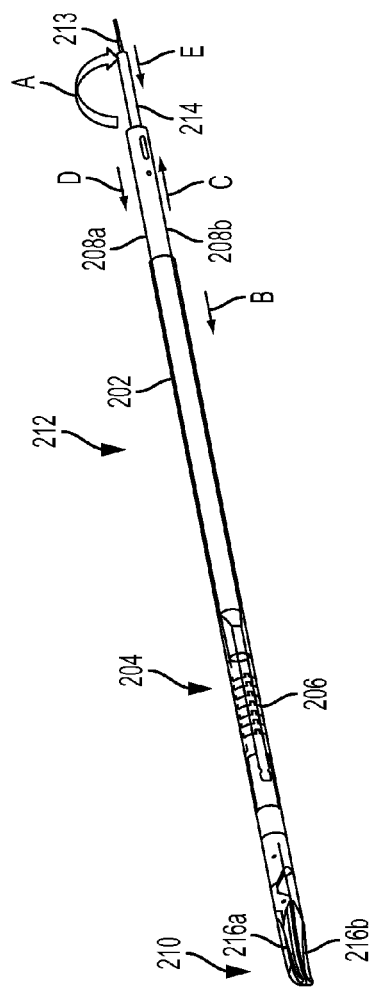
FIG. 6 is a perspective view of the shaft assembly and the end effector of the surgical instrument shown in FIGS. 1-3, illustrating the translation and rotational aspects of the shaft assembly, according to one embodiment.

FIG. 6 is a perspective view of the shaft assembly 212 and the end effector 210 of the surgical instrument 100, 101 shown in FIGS. 1-3, illustrating the translation and rotational aspects of the shaft assembly 212, according to one embodiment. As shown in the illustrated embodiment, the jaw members 216a, 216b of the end effector 210 are closed by pushing the outer tube 202 to advance it distally in direction B. The articulation joint 204 is articulated in a right-to-left counterclockwise direction by pushing the first articulation band 208a to advance it distally in direction C and the second articulation band 208b is pulled to retract it proximally in direction D. The articulation joint 204 can be articulated in a clockwise or left-to-right direction by reversing the forces applied to the articulation bands 208a, 208b. For example, by pulling the first articulation band 208a proximally and pushing the second articulation band 208b distally. The knife can be advanced distally when the jaw members 216a, 216b are closed by pushing the knife tube 214 to advance it distally in direction E'. The end effector 210 can be rotated counterclockwise in direction A as described in connection with FIG. 5 by rotatable the knife tube 214 counterclockwise in direction A'. The end effector 210 can be rotated clockwise by rotatable the knife tube 214 clockwise.

FIG. 7 is a sectional view of the articulation joint 204 of the shaft assembly 212 and end effector 210 of the surgical instrument 100, 101 shown in FIGS. 1-3, according to one embodiment. As illustrated in FIG. 7, the flexible neck 220 is located within the articulation joint 204 of the outer tube 202. The flexible neck 220 is flexible and enables the articulation joint 204 to articulate. As previously described, the articulation joint 204 includes a plurality of articulation sections 206 to enable the articulation joint 204 to articulate. The distal end of the spacer tube 217 is just proximal of the proximal end of the flexible neck 220. The hollow flexible knife cable 211 is located inside the flexible neck 220. The active rod 213 is located within the hollow flexible knife cable 211. The distal end of the hollow flexible knife cable 211 is fixedly coupled to the proximal end of the adapter 222 and the distal end of the adapter is fixedly coupled to the knife 224. The distal end of the active rod 213 is electrically couple to the electrical conductor 238. The non-rotatable closure ring 230 is located over the neck 240 of the second jaw member 216b and fixedly attached thereto by inserts 228a, 228b, which are connected in place to the circumferential groove 233 in the neck 240. As shown, the distal end of the outer tube 202 abuts a lip on the proximal end of the rotatable closure ring 232. Thus, when the outer tube 202 is advanced distally it acts on the rotatable closure ring 232 to close the first jaw member 216a.

The link 236 operatively couples the first jaw member 216a to the rotatable closure ring 232 via the first and second link pins 234a, 234b. The first link pin 234a is received though a proximal opening in the link 236 and an opening in the rotatable closure ring 232. The first link pin 234a rotatably couples the link 236 to the rotatable closure ring 232. The distal end of the link 236 defines another opening to receive the second link pin 234b. The second link pin 234b rotatably couples the first jaw member 216a to the link 236. The first jaw member 216a pivotally coupled to the pivot pin 252. Accordingly, as the outer tube 202 pushes distally on the rotatable closure ring 232, the first jaw member 216a closes shut. As the outer tube 202 is pulled proximally through the link 236 the first jaw member 216a opens.

FIG. 8 is sectional view of the outer tube 202, according to one embodiment. The illustrated view shows the outer tube 202 crimp tab 207b that is crimped onto the flexible neck 220 to fixedly couple the articulation joint 204 to the flexible neck 220. The first and second articulation bands 208a, 208b are located on either side of the flexible neck 220. The hollow flexible knife cable 217 is located over the adaptor 222, the knife 224, and the electrical conductor 238.

FIG. 9 is a sectional view of the outer tube 202 and the second jaw member 216b, according to one embodiment. As shown, the articulation bands 208a, 208b are located between the articulation sections 206 and the flexible neck 220. The articulation bands 208a, 208b are connected to the sides of the non-rotatable closure ring 230. The non-rotatable closure ring 230 is connected with inserts to the circumferential groove 233. Also shown is the hollow flexible knife cable 211 coupled to the adapter 222. The active rod 213 is positioned within the hollow flexible knife cable 211 and is electrically coupled to the electrical conductor 238. The electrical conductor 238 is covered by an electrically insulative sheath 221. The adapter 222 is fixedly coupled to the knife 224, which is slidably received within the non-rotatable closure ring 230, and the neck 240 portion of the second jaw member 216b. The rotatable closure ring 232 is slipped over the neck 240 of the second jaw member 216b and is secured to the link 236 and the first jaw member 216a by way of a link pin 234a as shown in FIG. 7.

With reference back to FIG. 9, the second jaw member 216b comprises a jaw electrode 254 that is electrically coupled to the active rod 213 via the electrical conductor 238. The jaw electrode 254 includes a slot 258 and the jaws 216a, 216b include as lot 256 to reciprocate a knife 224 therealong to sever tissue held between the jaw members 216a, 216b.

At least one stop member 259a, 259b, 259c may be disposed on either the first or second jaw member 216a, 216b, or both, to control the gap distance between the opposing jaw members 216a, 216b relative to one another. In the illustrated example, the stop members 259a, 259b, 259c are located on the second jaw member 216b and protrude through corresponding apertures formed in the jaw electrode 254. In the illustrated example, one stop member 259a is positioned at the distal end of the slot 258 and two stop members 259b, 259c are disposed laterally on either side of the slot 258.

The stop members 259a, 259b, 259c are formed from an electrically insulative material such as plastic, ceramic, glass, or any suitable electrically insulative material. The stop members 259a, 259b, 259c limit the movement of the two opposing jaw members 216a, 216b relative to one another. Preferably, the stop members 259a, 259b, 259c are made from an insulative material and are dimensioned to limit opposing movement of the jaw members 216a, 216b within a gap range (e.g., about 0.001 to about 0.006 inches) and apply a desired force to seal the tissue, at least one jaw member 216a, 216b.

FIGS. 10-13 illustrate a sequence of assembling the end effector 210 and internal shaft assembly 212, according to one embodiment. FIG. 10 is a perspective view of the end effector 210 portion of the surgical instrument 100, 101 shown in FIGS. 1-3 with the active rod 213 installed, according to one embodiment. The rotatable closure ring 232 is inserted over the neck 240 of the second jaw member 216b. The first link pin 234a is connected to the rotatable closure ring 232 through the link 236. The second link pin 234b is connected to the first jaw member 216a through the link 236. The pivot pin 252 is connected through the first and second jaw members 216a, 216b. The active rod 213 is then connected to the electrical conductor 238.

FIG. 11 is a perspective view of the end effector 210 portion of the surgical instrument 100, 101 shown in FIG. 10 with the adapter 222 and the hollow flexible knife cable 211 installed, according to one embodiment. The knife 224 is connected to the adapter 222 and then the adapter 222 is connected to the hollow flexible knife cable 211.

FIG. 12 is a perspective view of the end effector 210 portion of the surgical instrument 100, 101 shown in FIG. 11 with the non-rotatable closure ring 230 installed over the neck 240 of the second jaw member 216b, according to one embodiment. Once the non-rotatable closure ring 230 is slipped over the neck 240 the inserts 228a, 228b (not shown) are located through the slots 229a, 229b (not shown) formed on the non-rotatable closure ring 230 and are connected in place.

FIG. 13 is a perspective view of the end effector 210 portion of the surgical instrument 100, 101 shown in FIG. 12 with the flexible neck 220, knife tube 214, articulation bands 208a, 208b, and spacer tube 217 installed, according to one embodiment. The flexible neck 220 is slid over the hollow flexible knife cable 211. The knife tube 214 is connected to the hollow flexible knife cable 211. The spacer tube 217 is slid over the knife tube 214 and the hollow flexible knife cable 211. The articulation bands 208a, 208b are located over the spacer tube 217 and connected to the sides of the non-rotatable closure ring 230. Although not, shown, the outer tube 202 (FIGS. 4 and 6) is subsequently slid over the spacer tube 217 and crimped to the flexible neck 220 and the non-rotatable closure ring 230.

FIG. 14 is a detail view of the electrode 254 relative to the link 236, according to one embodiment. The link 236 operatively couples the rotatable closure ring 232 (not shown) to the first jaw element 216a (not shown) (see FIG. 7) via corresponding link pins 234a, 234b. The pivot pin 252 is employed to pivotally couple the first jaw element 216a to the second jaw element 216b (not shown). The jaw electrode 254 is electrically coupled to the electrical conductor 238, which is electrically coupled to the active rod 213 (not shown). The electrical conductor 238 is located lateral to the knife 224.

Figure 15:
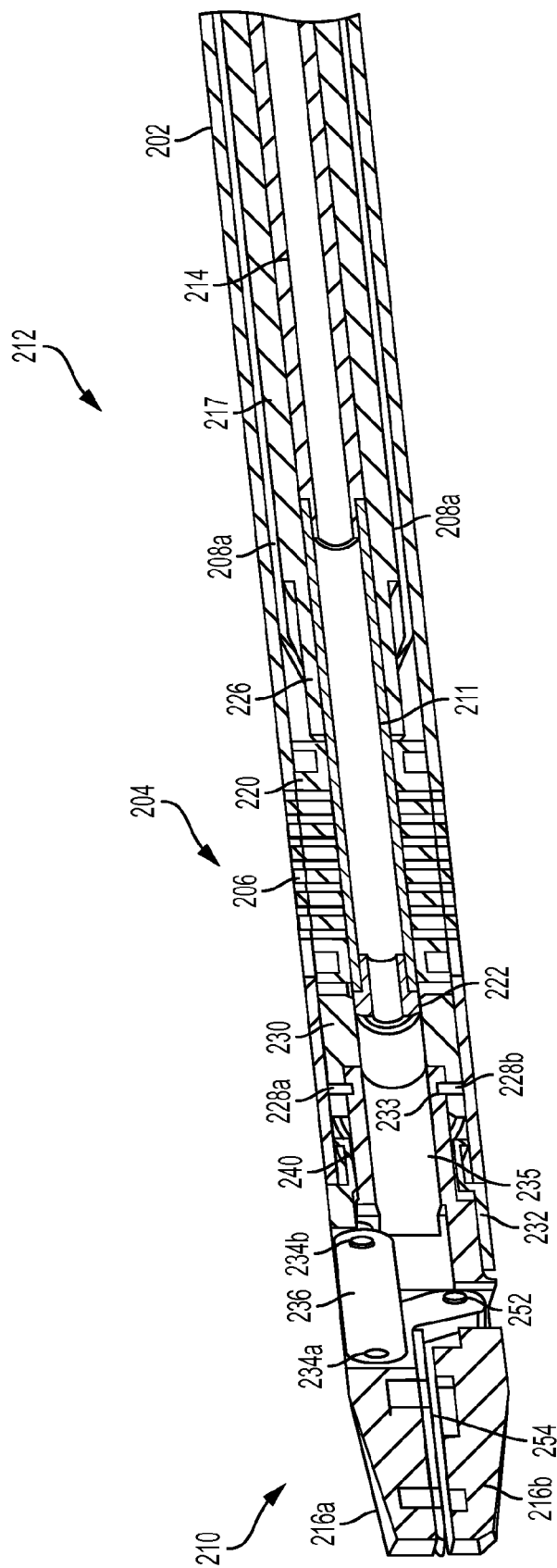
FIG. 15 is a sectional view of the shaft assembly and the end effector of the surgical instrument shown in FIGS. 1-3, according to one embodiment.

FIG. 15 is a sectional view of the shaft assembly 212 and the end effector 210 of the surgical instrument shown in FIGS. 1-3, according to one embodiment. This detailed view shows the one of the articulation tubes 208a located inside the outer tube 202. The spacer tube 217 is located inside the articulation band 208a. The knife tube is located inside the spacer tube 217 and is connected to the hollow flexible knife cable 211. The hollow flexible knife cable 211 is connected to the adapter 222. As previously discussed, the hollow flexible knife cable 211 is connected to the adapter 222 and to the knife tube 217. The spacer tube 217 guides the hollow flexible knife cable 211 and separates the knife tube 217 from the articulation bands 208a, 208b (not shown). The hollow flexible knife cable 211 slidably moves within the flexible neck 220 to allow the knife 224 (not shown) to advance while the articulation joint 204 is articulated. The adapter 22 and the knife 224 are slidably movable within the channel 235 defined by the non-rotatable closure ring 230 and the neck 240 of the second jaw element 216b. The non-rotatable closure ring 230 is connected to the neck 240 by inserts 228a, 228b connected to the circumferential groove 233 on the neck 240. The first jaw element 216a is operatively coupled to the rotatable closure ring 232 via the link 236 and link pins 234a, 234b. The first jaw element 216a is pivotally coupled to the second jaw element 216b via the pivot pin 252.

FIG. 16 is a partial exploded view showing the assembly of the end effector 210 and the shaft assembly 212 of the surgical instrument 100, 101 shown in FIGS. 1-3, according to one embodiment. The electrical conductor 238 is fed through the hollow portion of the neck 240 and the jaw electrode 254 is located in place on the second jaw element 216b. The first jaw element 216a is then coupled to the second jaw element 216b by inserting the pivot pin 252 through a hole 270 in the second jaw element 216b and another hole 264 in the first jaw element 216a. The pivot pin 252 is then connected to the second jaw element 216. The distal end of the link 236 is then inserted into a slot 260 defined on the first jaw element 216a. The second link pin 234b is inserted through a hole 262 defined in the first jaw element 216a and through a hole 266 defined at the distal end of the link 236. The second link pin 234b is then connected to the first jaw element 216a.

The distal end of the hollow flexible knife cable 211 is attached to the adapter 222 which is then attached to the proximal end of the knife 224. The active rod 213 is inserted through the hollow flexible knife cable 211 and the adapter 222. The active rod 213 is then fed through the non-rotatable closure ring 230 and the rotatable closure ring 232 and the distal end of the active rod 213 is electrically coupled to the electrical conductor 238.

The rotatable closure ring 232 is then slipped over the neck 240 while the proximal end of the link 236 is located in a slot 243 defined by the rotatable closure ring 232. The first link pin 234a is then inserted through a hole 274 defined in rotatable closure ring 232 and a hole 268 defined at the proximal end of the link 236. The first link pin 234a is then connected to the rotatable closure ring 232.

The non-rotatable closure ring 230 is then slipped over the neck 240 until the slots 229a, 229b (not shown) are aligned with the groove 233 defined on the neck 240. The inserts 228a, 228b are then inserted through the slots 229a, 229b (not shown) such that they catch the groove 233. The inserts slots 228a, 228b are then connected to the non-rotatable closure ring 230 and the neck 240.

FIG. 17 is a final assembly of the end effector 210 and the shaft assembly 212 of the surgical instrument shown in FIGS. 1-3, according to one embodiment. The outer tube 202 is slipped over the subassembly shown in FIG. 13. The outer tube is attached to the flexible neck 220 (not shown) with crimp tabs 207a, 207b. The outer tube 202 is also attached to the non-rotatable closure ring 230 (not shown) with crimp tab 215.

FIG. 18 is a view of the end effector 210 and shaft assembly 212 of the surgical instrument 100, 101 shown in FIGS. 1-3 in an articulated position and the jaws in an open position, according to one embodiment. In the illustrated embodiment, the shaft assembly 212 is in an articulated position at about 55 degrees of articulation. More articulation may be provided by adding articulation sections 206. As previously discussed, additional articulation sections 206 provide a smaller radius of curvature of the articulation joint 204. Less articulation may be provided by removing articulation sections 206. As previously discussed, fewer articulation sections 206 provide a larger radius of curvature of the articulation joint 204. To close the jaw elements 216a, 216b while the outer tube 202 is articulated, the outer tube 202 is pushed forward in direction G such that the entire articulation joint 204 moves forward in direction G. As previously discussed, the outer tube 202 acts on the rotatable closure ring 232 to push on the link 236 and close the first jaw element 216a towards the second jaw element 216b. The knife 224 (not shown) is fired by advancing the knife tube 214 (not shown) in a distal direction G. The knife 224 (not shown) can be fired while the jaws are closed and the shaft assembly 212 is articulated due in part to the flexible neck 230 (not shown) and the hollow flexible knife cable 211 (not shown).

FIG. 19 is a view of the end effector 210 and shaft assembly 212 of the surgical instrument 100, 101 shown in FIGS. 1-3 in an articulated position and the jaws in an open position, according to one embodiment. In the illustrated embodiment, the shaft assembly 212 is in an articulated position at about 55 degrees of articulation. The end effector 210 section beyond the articulation joint 204 can be rotated in direction A or in an opposite direction by rotatable the knife tube 214 (not shown).

Figure 20:
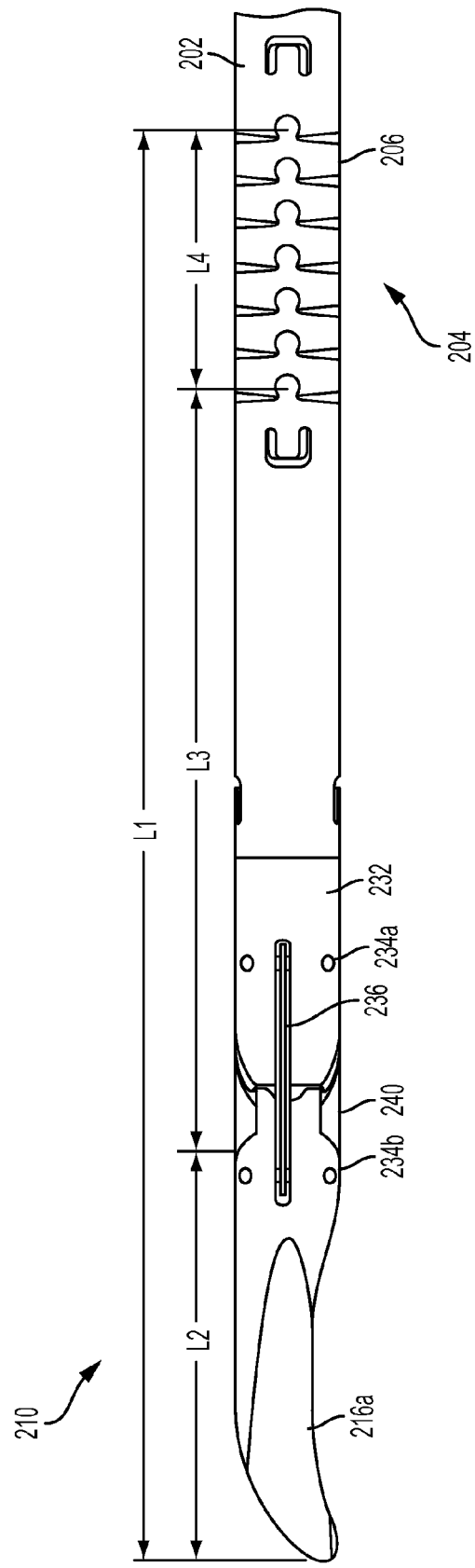
FIG. 20 is a side view of the end effector and shaft assembly of the surgical instrument shown in FIGS. 1-3 with the jaws closed defining example dimensions, according to one embodiment.

FIG. 20 is a side view of the end effector 210 and shaft assembly 212 of the surgical instrument 100, 101 shown in FIGS. 1-3 with the jaws closed defining example dimensions, according to one embodiment. As shown, various dimensions are disclosed, without limitation. In one embodiment, the length L1 of the section extending between the distal tip of the jaw elements 216a, 216b to the most proximal articulation section 206 is about 2.96 in. The length L2 of the jaw elements is about 0.865 in. The length L3 of the section extending from a proximal end of the jaw elements 216a, 216b to the most distal articulation section 206 is about 1.6 in. The length L4 of the articulation joint 204 is about 0.54 in. Other dimensions can be substituted, for example.

Figure 21:
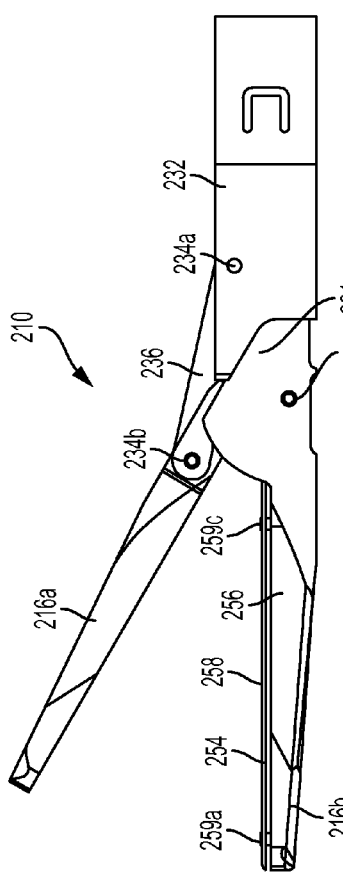
FIG. 21 shows the end effector with the first jaw element in an open position, according to one embodiment.
Figure 22:
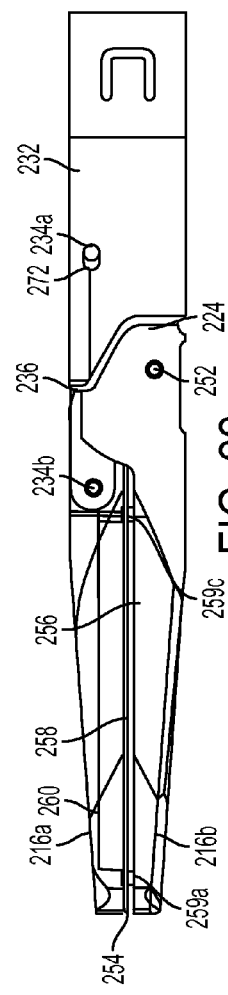
FIG. 22 shows the end effector with the first jaw element in a closed position, according to one embodiment.
Figure 23:
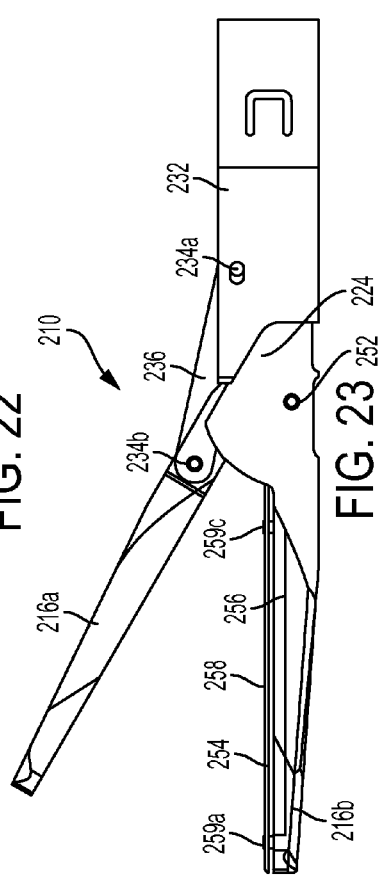
FIG. 23 shows the end effector with the first jaw element transitioning to an open position, according to one embodiment.

FIGS. 21-23 illustrate a sequence of closing and opening the jaw elements 216a, 216b of the surgical instrument 100, 101 shown in FIGS. 1-3, according to one embodiment. FIG. 21 shows the end effector 210 with the first jaw element 216a in an open position, according to one embodiment. When closing the jaw element 216a, the rotatable closure ring 232 pushes on the first jaw element 216a to close it. This maximizes the mechanical advantage when closing the first jaw element 216a.

FIG. 22 shows the end effector 210 with the first jaw element 216a in a closed position, according to one embodiment. A slot 272 in the link 236 allows the link 236 to pull open but not push closed.

FIG. 23 shows the end effector 210 with the first jaw element 216a transitioning to an open position, according to one embodiment. When opening the first jaw element 216a the link 236 pulls the jaw element 216a open. This maximizes the mechanical advantage when opening.

FIGS. 24-33 illustrate various embodiments of electrosurgical instruments comprising an articulating shaft with a jaw pull mechanism. In one embodiment, the electrosurgical instrument comprises an articulating bipolar RF device with jaws, articulation bands, and a combination of an internal flexible guide and an external laser cut outer tube to form an articulation joint. In one embodiment, the electrosurgical instrument comprises pull bands that are disposed central to the shaft and above a knife. An outer tube may be crimped to hold the jaw and flexible guide in place. In one embodiment, the electrosurgical instrument comprises a knife push tube located internal to the knife external tube to attach to handle mechanisms. In various embodiments, the present disclosure provides electrosurgical instruments that comprise a combination of some or all of these features without limitation.

In connection with the embodiments of the electrosurgical instrument described in FIGS. 24-33, the articulation mechanism can provide up to 55 degrees of articulation. The pull bands and knife can be centrally located within the outer tube to reduce articulation effect on the knife and the jaw pull position. Assembly of the electrosurgical instrument may be easier than conventional articulating devices. Embodiments of the electrosurgical instrument comprise reduced joint to jaw length and larger jaw than current device. Embodiments of the electrosurgical instrument provide improved dissection and grasping. Embodiments of the electrosurgical instrument enable tissue sealing prior to tissue dissection or cutting.

FIG. 24 is a perspective view of a shaft assembly 312 in an articulated position and an end effector 310 with jaw members 316a, 316b in an open position, according to one embodiment. FIG. 25 is a perspective view of the shaft assembly 312 and end effector 310 shown in FIG. 24 in an unarticulated (straight) position with the jaw members 316a, 316b in a closed position, according to one embodiment. The shaft assembly 312 and the end effector 310 may be employed in a surgical instrument similar to the surgical instruments 100, 101 shown in FIGS. 1-3. FIG. 24 illustrates the translation and rotational aspects of the shaft assembly 312, according to one embodiment.

In some embodiments, the end effector 310 is coupled to the distal end of the shaft assembly 312. The end effector 310 comprises first and second jaw members 316a, 316b. The first jaw member 316a is pivotally coupled to the second jaw member 316b. The first jaw member 316a is pivotally moveable with respect to the second jaw member 316b to grasp tissue therebetween. The first jaw member 316a may be referred to as the upper jaw or upper jaw member. In some embodiments, the second jaw member 316b is fixed. The second jaw member 316b may be referred to as the lower jaw or lower jaw member. In other embodiments, the first jaw member 316a and the second jaw member 316b are pivotally movable. In one example, at least one of the jaw members 316a, 316b is fixed relative to the shaft assembly 312 assembly. In another example both jaw members 316a, 316b are movable relative to the shaft assembly 312. In the illustrated example, the first jaw member 316a is movable relative to shaft assembly 312 and the second jaw member 316b is fixed relative to the shaft assembly 312. The jaw members 316a, 316b are movable relative to one another from a first, open position to a second, closed position for grasping tissue therebetween. As shown in the embodiment illustrated in FIGS. 24 and 25, the jaw members 316a, 316b of the end effector 310 can be closed by pulling the jaw tube 314 proximally in direction F and are closed by pushing the jaw tube 314 in an opposite direction distally in direction F'. It should be noted that this functionality is opposite that of the embodiment described in connection with FIGS. 4-23 where the outer tube is pushed distally to close the jaw elements. At least one jaw member 316a, 316b and the jaw electrode 354 comprise slots 356, 358 or knife channels to reciprocate a knife therealong and sever tissue grasped between the first and second jaw members 316a, 316b.

At least one of the jaw members 316a, 316b is adapted to connect to an electrosurgical energy source such that electrosurgical energy may be selectively communicated through tissue held between the jaw members 316a, 316b to effect a tissue seal. At least one of the jaw members 316a, 316b of the end effector 310 comprises at least one electrode adapted to connect to an electrosurgical energy source and configured to deliver energy to tissue held between the jaw members 316a, 316b to effect a tissue a seal. Energy delivered by the electrode may comprise, for example, radiofrequency (RF) energy, sub-therapeutic RF energy, ultrasonic energy, and/or other suitable forms of energy, either independently or in combination. In some embodiments, a cutting member (not shown) is receivable within a longitudinal slot defined by the first jaw member 316a and/or the second jaw member 316b. The cutting member is configured to cut tissue grasped between the first jaw member 316a and the second jaw member 316b. In some embodiments, the cutting member comprises an electrode for delivering energy, such as, for example, RF, ultrasonic energy, or a combination thereof that can be delivered independently or in combination.

As further illustrated in FIG. 25, the articulation section 304 of the shaft assembly 312 is articulated in a right-to-left counterclockwise direction or a left-to-right clockwise direction by actuating articulation bands 308a, 308b slidably positioned between the articulation joints 306 and the flexible neck 320 (FIGS. 26-27). The articulation section can be articulated in a clockwise direction by pulling on the first articulation band 308a to retract it proximally in direction C and pushing on the second articulation band 308b to advance it distally in direction D'. The articulation section 304 can be articulated in a counterclockwise direction by reversing the forces applied to the first and second articulation bands 308a, 308b. For example, by pushing the first articulation band 308a to advance it distally in direction C' and by pulling the second articulation band 308b to retract it proximally in direction D. It should be noted that the articulation section 304 of the shaft assembly 312 can be articulated clockwise or counterclockwise regardless of whether the jaw members 316a, 316b are opened or closed.

The knife is slidably movable distally and proximally by actuating the knife tube 317. When the jaw members 316a, 316b are closed, the knife can be advanced to cut tissue clamped between the jaw members 316a, 316b by pushing the knife tube 317 distally in direction E'. The knife can be retracted by pulling knife tube 317 proximally in direction E.

The end effector 310 is rotatable in a clockwise or counterclockwise direction by rotatable the knife tube 317 in a similar direction. For example, the end effector 310 can be rotated clockwise by rotatable the knife tube 317 clockwise and the end effector 310 can be rotated counterclockwise by rotatable the knife tube 317 counterclockwise. It should be noted that the end effector 310 can be rotated in either direction regardless of whether the jaw members 316a, 316b are in an open or a closed position.

Energy is delivered to a jaw electrode located in the end effector 310 though an active rod 313 positioned within the jaw tube 314. The active rod is electrically coupled on the proximal end to an energy source and on a distal end is electrically coupled to an electrical conductor 328, which is electrically coupled to the jaw electrode. The second jaw member 316b comprises a jaw electrode 354 that is coupled to the active rod 313 via the electrical conductor. The jaw electrode 354 includes a slot 358 to receive the knife. The knife is advanced by advancing the knife tube 317 distally in direction E' and is retracted proximally by pulling the knife tube 317 in direction E.

FIG. 26 is a sectional view of the shaft assembly 312 and end effector 310, according to one embodiment. The outer tube 302 slidably receives the articulation bands 308a, 308b (not shown in this view), the knife tube 317, and the jaw tube 314. The active rod 313 is located within the jaw tube 314 and is electrically coupled to an electrode 328, which is electrically coupled to the jaw electrode 354. The jaw tube 314 is connected to one of two jaw actuation bands 315a, 315b (not shown in this view), which runs down the length of the shaft assembly 312 to the end effector 310 where it is pivotally coupled to a first link 338a by a pin 334. The first link 338a is pivotally coupled to the first jaw element 316a by a pin 336, which is rotatably coupled to the outer tube 302 by a pin 352. The pins 334, 336, 352 are fixedly coupled to the outer tube 302. Accordingly, as the jaw tube 314 is pulled proximally in direction F the jaw actuation band 315a is pulled proximally, the first jaw element 316a moves towards the second jaw element 316b to a closed position. With the jaw elements 316a, 316b in a closed position, the jaw elements 316a, 316b are opened by pushing distally on the jaw tube 314 in direction F'. As previously mentioned, the knife 324 is connected to the knife tube 317 such that the knife 324 is advanced distally by pushing on the knife tube 317 in direction E' and the knife 324 is retracted proximally by pulling on the knife tube 317 in direction E.

FIG. 27 is a sectional view of the shaft assembly 312 and end effector 310, according to one embodiment. As shown in FIG. 27, the dual jaw actuation bands 315a, 315b are slidably received within a slot 319 defined in the flexible neck 320 portion of the articulation section 304 of the shaft assembly 312. The electrode 328 is located below one jaw actuation band 315a and the knife 324 is located below the other jaw actuation band 315b. The electrode 328 is laterally disposed from the knife 324 and below the other jaw actuation band 315a. The electrical conductor 328 is covered by an electrically insulative sheath 321.

FIG. 28 is a longitudinal sectional view of the shaft assembly 312, according to one embodiment. As illustrated in FIG. 28, the articulation band 308a is slidably received within the outer tube 302 and the knife tube 317 is slidably received within the articulation band 308a. The jaw tube 314 is also shown extending longitudinally within the knife tube 317 and coupled to the right jaw actuation band 315a. The knife 324 is coupled to the knife tube 317 and reciprocates within the knife channel. The knife 324 is advanced distally by pushing on the knife tube 317 in direction E'. The knife 324 is retracted proximally by pulling on the knife tube 317 in direction E. The knife 324 comprises a coupling members 325a, 325b that couple the knife 324 to the knife tube 317 by locating the proximal coupling member 325b through a slot 323 defined in the knife tube 317.

The electrical conductor 328, which is electrically coupled to the jaw electrode 354 (FIGS. 24-26), is covered by an electrically insulative sheath 321. The electrical conductor 328 is electrically coupled to the active rod 313, which also is covered by an electrically insulative sheath 327. The active rod 313 is adapted to connect to an electrosurgical energy source and configured to deliver energy to tissue held between the jaw members 316a, 316b to effect a tissue a seal. The electrosurgical energy source may comprise, for example, a radiofrequency (RF) energy source, a sub-therapeutic RF energy source, an ultrasonic energy source, and/or other suitable energy sources. Where multiple energy sources are used, the energy may be delivered either independently or in combination.

Figure 29:
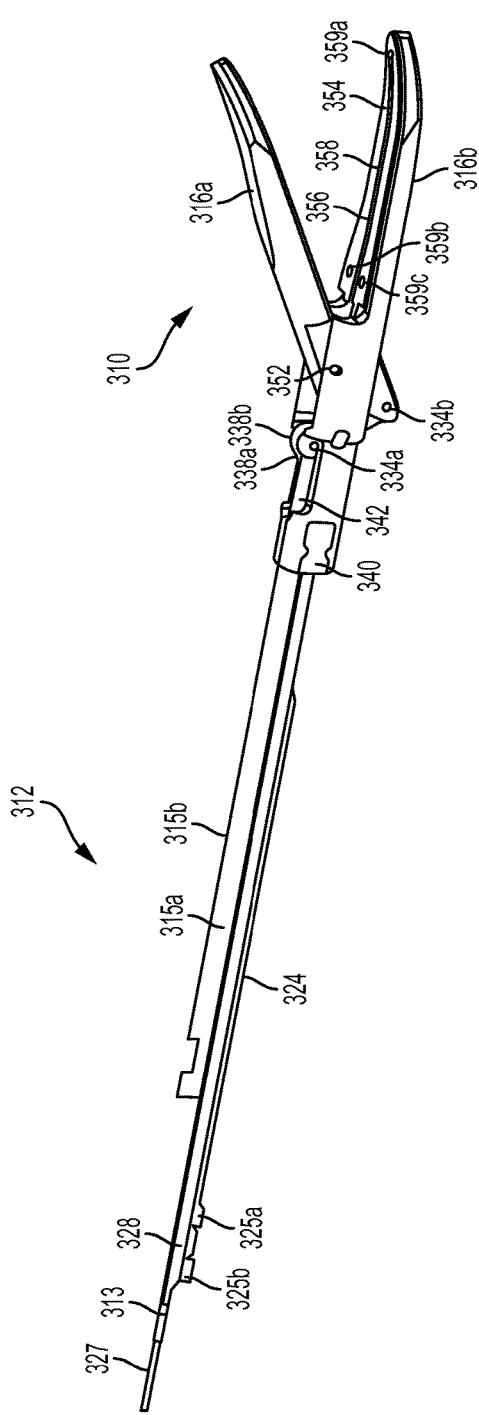
FIG. 29 is a perspective view of the shaft assembly and end effector portions of one embodiment of the surgical instruments shown in FIGS. 1-3, according to one embodiment.

FIG. 29 is a perspective view of the shaft assembly 312 and end effector 310 portions of one embodiment of the surgical instruments 100, 101, according to one embodiment. In the view shown in FIG. 29, the outer tube 302, the knife tube 314, and the articulation bands 308a, 308b of the shaft assembly 312 are removed to better see the active rod 313, the knife 324, the electrical conductor 328, the jaw actuation bands 315a, 315b, and the end effector 310 actuation mechanism. The active rod 313 is connected to the electrical conductor 328. The jaw actuation bands 315a, 315b are operatively coupled to proximal portions of corresponding first and second linkages 338a, 338b. The distal ends of the linkages 338a, 338b are coupled to the first jaw member 316a. A pin 334a is located between the proximal ends of the linkages 338a, 338b and the jaw actuation bands 315a, 315b. Another pin 334b is located between distal ends of the linkages 338a, 338b and the proximal end of the jaw member 316a. Yet another pin 352 is located between the first and second jaw members 316a, 316b. The pins 334a, 334b, and 352 are connected in place.

The first, movable, jaw member 316a is pivotally movable about the pivot pin 352 relative to the second, fixed, jaw member 316b between open and closed positions. The first jaw member 316a is movable relative to the second jaw member 316b by actuating the jaw actuation bands 315a, 315b. For example, as the jaw actuation bands 315a, 315b are pushed distally, the proximal end of the linkages 338a, 338b and the pin 334a slide distally in a slot 342 defined in the neck section 340 of the second jaw member 316b. As the proximal end of the linkages 338a, 338b translate distally in the slot 342, the distal end of the linkages 338a, 338b are driven in a downwardly direction and cause the first jaw member 316a to pivot about the pivot pin 352 to an open position as shown in FIG. 29. To grasp tissue, the first jaw member 316a is closed onto the second jaw member 316b by pulling on the jaw actuation bands 315a, 315b to drive them in a proximal direction. Accordingly, the proximal end of the linkages 338a, 338b and the pin 334a slide proximally in the slot 342 casing the linkages 338a, 338b to straighten and cause the first jaw member 316a to rotate about the pivot pin 352 to a closed position.

The bottom or second jaw member 316b includes an electrode 354 to deliver energy to tissue grasped between the first and second members 316a, 316b. The electrode 354 is electrically coupled to the electrical conductor 328 which is electrically coupled to the active rod 313. As previously discussed the active 313 is adapted to couple to an energy source and acts as one pole of the electrical circuit. The first jaw member 316a is coupled to a second pole of the electrical circuit. Thus, when tissue is grasped between the first and second jaw members 316a, 316b energy can be applied to the tissue to effect a seal. The end effector 310 includes at least one stop member 359a, 359b, 359c may be disposed on either the first or second jaw member 316a, 316b, or both, to control the gap distance between the opposing jaw members 316a, 316b relative to one another. In the illustrated example, the stop members 359a, 359b, 359c are located on the second jaw member 316b and protrude through corresponding apertures formed in the jaw electrode 354. In the illustrated example, one stop member 359a is positioned at the distal end of the slot 358 and two stop members 359b, 359c are disposed laterally on either side of the slot 358.

The stop members 359a, 359b, 359c are formed from an electrically insulative material such as plastic, ceramic, glass, or any suitable electrically insulative material. The stop members 359a, 359b, 359c limit the movement of the two opposing jaw members 316a, 316b relative to one another. Preferably, the stop members 359a, 359b, 359c are made from an insulative material and are dimensioned to limit opposing movement of the jaw members 316a, 316b within a gap range (e.g., about 0.001 to about 0.006 inches) and apply a desired force to seal the tissue, at least one jaw member 316a, 316b. Once the tissue is sealed, the knife 324 is configured to reciprocate within the slots 356, 358 to sever the tissue.

Figure 30:
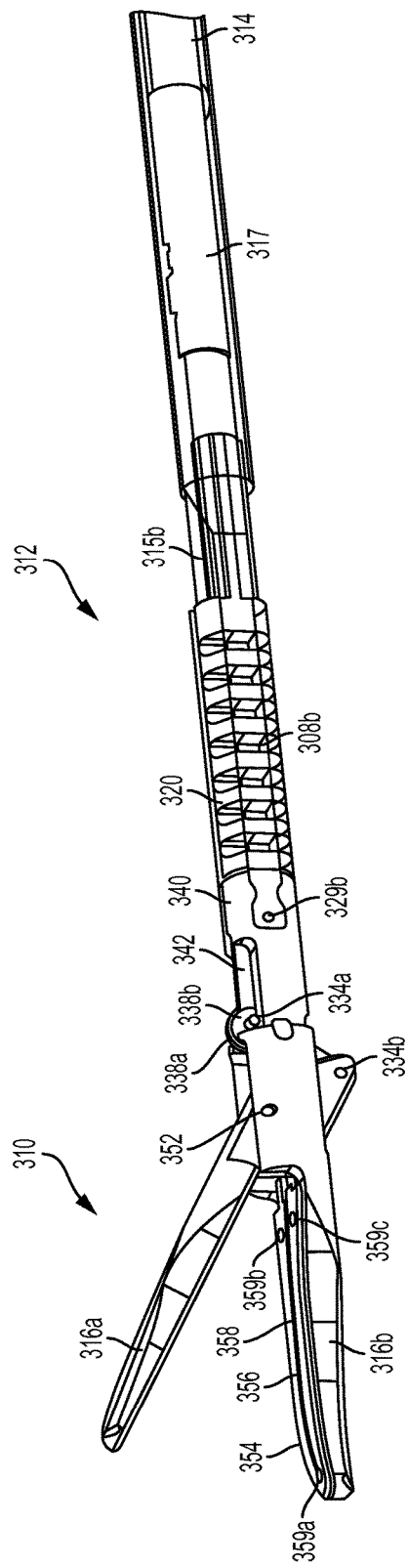
FIG. 30 is a perspective view of the shaft assembly and end effector portions of one embodiment of the surgical instruments shown in FIGS. 1-3, according to one embodiment.

FIG. 30 is a perspective view of the shaft assembly 312 and end effector 310 portions of one embodiment of the surgical instruments 100, 101, according to one embodiment. In the view shown in FIG. 30 the jaw tube 314, the knife tube 317, the flexible neck 320, and the articulation bands 308a, 308b portions of the shaft assembly 312 are shown to describe the operation thereof. With reference now to both FIGS. 29 and 30, the shaft assembly 312 may be assembled by sliding the flexible neck 320 over knife 324, the actuation bands 315a, 315b, and the electrical conductor 328. The knife 320 is connected to the knife tube 317 and the jaw tube 314 is connected to the actuation bands 315a,315b. The articulation bands 308a, 308b are connected to the lateral portions of the neck section 340 of the second jaw element 316b by pins. As shown in FIG. 30, the articulation band 308b is connected to one side of the neck section 340 of the second jaw element 316b by a pin 329b. Although not shown, the articulation band 308a is connected to the other side of the neck section 340 of the second jaw element 316b by another pin. As previously discussed, connections may be made by any suitable means of attachment by a weld, braze, solder, bond, glue, rivet, screw, bolt, crimp, or other suitable means.

Figure 31:
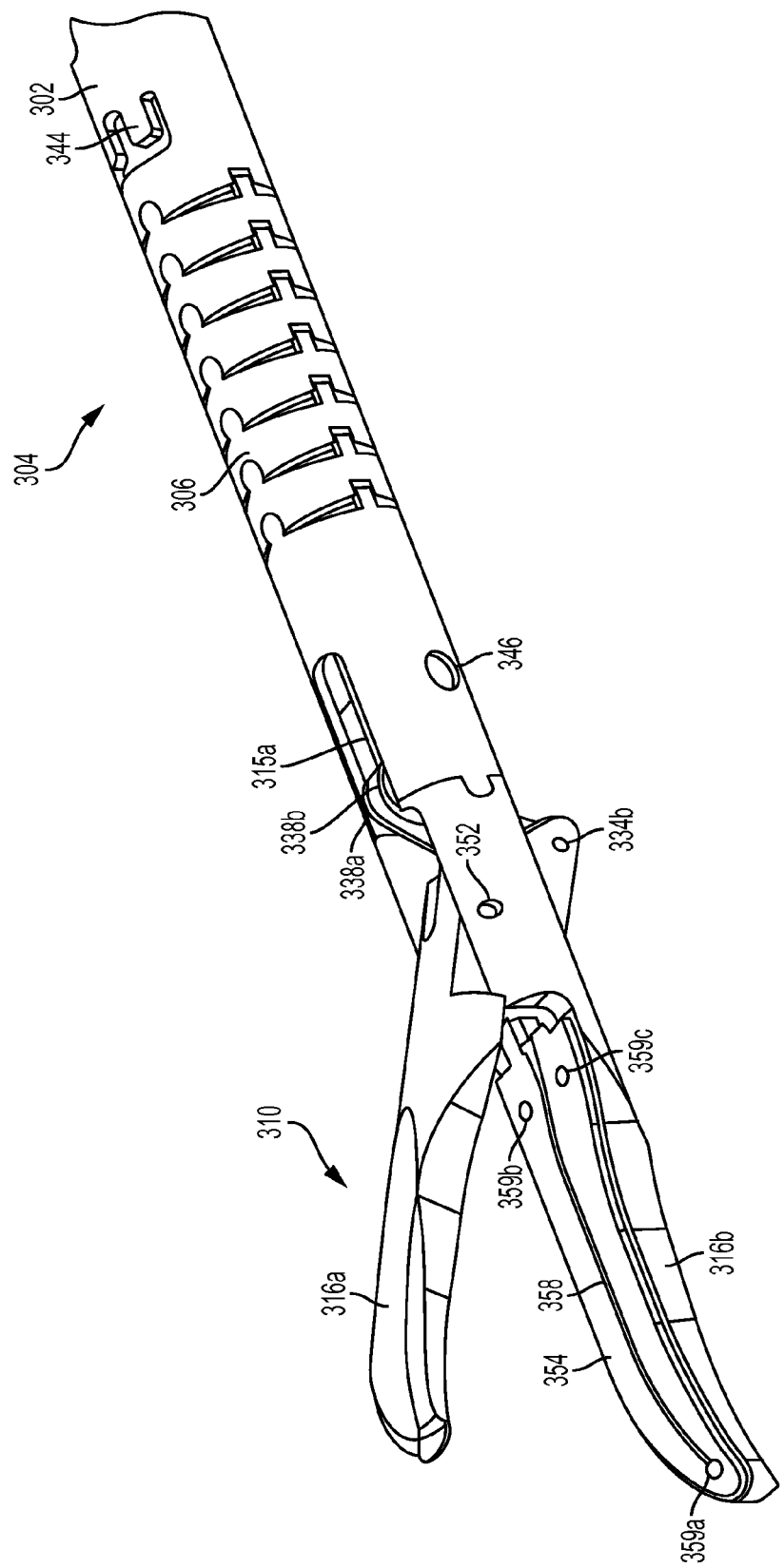
FIG. 31 is a perspective view of the shaft assembly and end effector sections of one embodiment of the surgical instruments shown in FIGS. 1-3, according to one embodiment.

FIG. 31 is a perspective view of the shaft assembly 312 and end effector 310 sections of one embodiment of the surgical instruments 100, 101, according to one embodiment. In the view shown in FIG. 31, the outer tube 302 including the articulation joints 306 are slid over the underlying components. The flexible neck 320 is attached to the outer tube 304, for example, by a crimp 344. The lower jaw 316b is attached to the outer tube 302, for example, by a weld or crimp 346.

Figure 32:
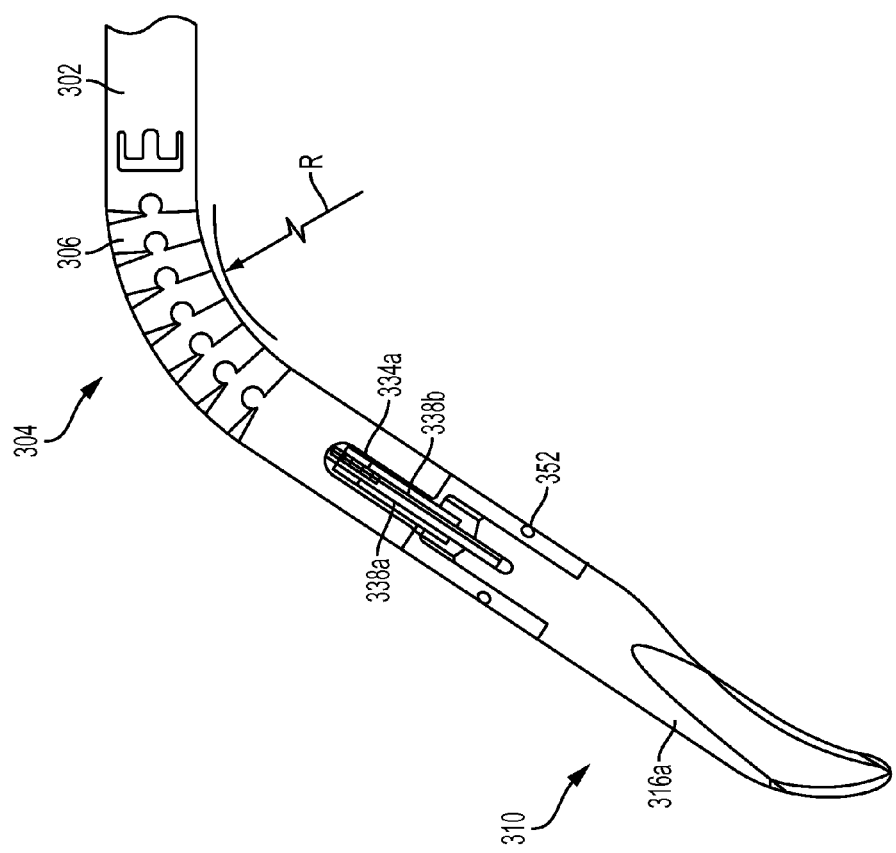
FIG. 32 illustrates the shaft assembly of one embodiment of the surgical instruments shown in FIGS. 1-3, in an articulated position, according to one embodiment.

FIG. 32 illustrates the shaft assembly 312 of one embodiment of the surgical instruments 100, 101, in an articulated position according to one embodiment. In the illustrated example, the shaft assembly 312 is shown at 55 degrees of articulation in one direction. The shaft assembly 312 can be articulated +/−55 degrees from a straight position by pulling and pushing on corresponding articulation bands 308a, 308b. For example, starting from a straight position at 0 degrees, the shaft assembly 312 can be articulated between 0 degrees and +55 degrees, and any intermediate position thereof, by pulling on the right articulation band 308a and pushing on the left articulation band 308b. Likewise, starting from a straight position at 0 degrees, the shaft assembly 312 can be articulated between 0 degrees and −55 degrees, and any intermediate position thereof, by pulling on the right articulation band 308a and pushing on the left articulation band 308b.

Figure 33:
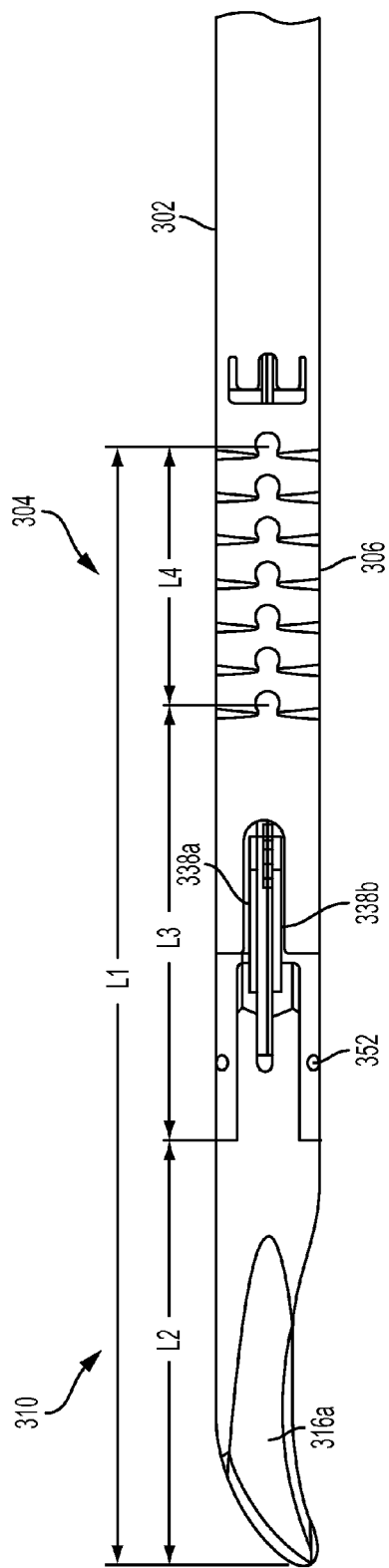
FIG. 33 is a side view of the end effector and shaft assembly of the surgical instruments shown in FIGS. 1-3 with the jaws closed defining example dimensions, according to one embodiment.

FIG. 33 is a side view of the end effector 310 and shaft assembly 312 of the surgical instrument 100, 101 shown in FIGS. 1-3 with the jaws closed defining example dimensions, according to one embodiment. As shown, various dimensions are disclosed, without limitation. In one embodiment, the length L1 of the section extending between the distal tip of the jaw elements 316a, 316b to the most proximal articulation joint 306 is about 2.27 in. The length L2 of the jaw elements is about 0.865 in. The length L3 of the section extending from a proximal end of the jaw elements 316a, 316b to the most distal articulation joint 306 is about 0.88 in. The length L4 of the articulation section 304 is about 0.54 in. Other dimensions can be substituted, for example.

It is worthy to note that any reference to "one aspect," "an aspect," "one embodiment," or "an embodiment" means that a particular feature, structure, or characteristic described in connection with the aspect is included in at least one aspect. Thus, appearances of the phrases "in one aspect," "in an aspect," "in one embodiment," or "in an embodiment" in various places throughout the specification are not necessarily all referring to the same aspect. Furthermore, the particular features, structures or characteristics may be combined in any suitable manner in one or more aspects.

Although various embodiments have been described herein, many modifications, variations, substitutions, changes, and equivalents to those embodiments may be implemented and will occur to those skilled in the art. Also, where materials are disclosed for certain components, other materials may be employed. It is therefore to be understood that the foregoing description and the appended claims are intended to cover all such modifications and variations as falling within the scope of the disclosed embodiments. The following claims are intended to cover all such modification and variations.

Although various embodiments have been described herein, many modifications, variations, substitutions, changes, and equivalents to those embodiments may be implemented and will occur to those skilled in the art. Also, where materials are disclosed for certain components, other materials may be employed. It is therefore to be understood that the foregoing description and the appended claims are intended to cover all such modifications and variations as falling within the scope of the disclosed embodiments. The following claims are intended to cover all such modification and variations.

The invention claimed is:

1. An electrosurgical instrument, comprising:
   an end effector comprising a first jaw member and a second jaw member, the first and second jaw members being movable relative to one another from a first, open position to a second, closed position for grasping tissue therebetween, wherein at least one of the first and second jaw members is adapted to connect to an electrosurgical energy source such that electrosurgical energy may be selectively communicated through tissue held between the first and second jaw members to effect a tissue seal;
   at least one of the first or second jaw members including a knife channel defined therein configured to reciprocate a knife therealong for severing tissue held between the first and second jaw members; and
   a two-stage articulation joint coupled to the end effector, the two-stage articulation joint operatively coupled to first and second articulation bands configured to articulate the end effector, the two-stage articulation joint comprising:
      an outer cut metal tube comprising a plurality of articulation sections with hinge and locking features that closes and opens the first and second jaw members; and
      a solid but flexible inner core positioned within the outer cut metal tube;
   a non-rotatable closure ring coupled to a distal end portion of the outer cut metal tube;
   a rotatable closure ring, wherein a proximal end portion of the rotatable closure ring is coupled to the non-rotatable closure ring; and
   a closure link having a distal end portion and a proximal end portion,
   wherein the proximal end portion of the closure link is coupled to the rotatable closure ring and the distal end portion of the closure link is coupled to one of the first and second jaw members,
   wherein the rotatable closure ring and the closure link are configured to close and open the end effector,
   wherein the rotatable closure ring is rotatable relative to the non-rotatable closure ring and the outer cut metal tube, which allows the rotatable closure ring to rotate independently of the non-rotatable closure ring and the outer cut metal tube while a longitudinal movement of the rotatable closure ring and the non-rotatable closure ring is synchronized,
   wherein the rotation of the rotatable closure ring relative to the non-rotatable closure ring and the outer cut metal tube results in a rotation of the first and second jaw members, which allows the first and second jaw members to rotate independently of the non-rotatable closure ring and the outer cut metal tube.

2. The electrosurgical instrument of claim 1, wherein the closure link is configured to pull the at least one of the first or second jaw members open relative to the other jaw member and the rotatable closure ring is configured to push the at least one of the first or second jaw members closed relative to the other jaw member.

3. The electrosurgical instrument of claim 1, wherein the end effector is configured to simultaneously rotate and articulate.

4. The electrosurgical instrument of claim 3, wherein the end effector is configured to rotate when the end effector is in an articulated position.

5. The electrosurgical instrument of claim 1, further comprising a knife configured to reciprocate within the knife channel and rotate when the end effector is rotated.

6. The electrosurgical instrument of claim 5, further comprising a flexible hollow cable and a knife tube, wherein the flexible hollow cable is coupled between the knife and the knife tube such that the knife can be pushed through at least one of the plurality of articulation sections and wherein the flexible hollow cable is located over an electrical conductor.

7. The electrosurgical instrument of claim 1, further comprising a rotatable pivot, wherein the first and second articulation bands are coupled to at least one of the first or second jaw members through the rotatable pivot.

8. An electrosurgical instrument, comprising:
   an end effector comprising a first jaw member and a second jaw member, the first and second jaw members being movable relative to one another from a first, open position to a second, closed position for grasping tissue therebetween, wherein at least one of the first and second jaw members is adapted to connect to an electrosurgical energy source such that electrosurgical energy may be selectively communicated through tissue held between the first and second jaw members to effect a tissue seal;
   at least one of the first or second jaw members including a knife channel defined therein configured to reciprocate a knife therealong for severing tissue held between the first and second jaw members;
   a non-rotatable closure ring;
   a rotatable closure ring, wherein a proximal end portion of the rotatable closure ring is coupled to the non-rotatable closure ring; and
   a closure link having a distal end portion and a proximal end portion,
   wherein the proximal end portion of the closure link is coupled to the rotatable closure ring and the distal end portion of the closure link is coupled to one of the first and second jaw members,
   wherein the rotatable closure ring and the closure link are configured to close and open the end effector,
   wherein the rotatable closure ring is rotatable relative to the non-rotatable closure ring, which allows the rotatable closure ring to rotate independently of the non-rotatable closure ring while a longitudinal movement of the rotatable closure ring and the non-rotatable closure ring is synchronized,
   wherein the rotation of the rotatable closure ring relative to the non-rotatable closure ring results in a rotation of the first and second jaw members, which allows the first and second jaw members to rotate independently of the non-rotatable closure ring.

9. The electrosurgical instrument of claim 8, wherein the rotatable closure ring is configured to transmit a closure force to the first and second jaw members while the first and second jaw members are rotated relative to an outer tube at any angle.

10. The electrosurgical instrument of claim 8, further comprising a knife configured to reciprocate within the knife channel and rotate when the end effector is rotated.

11. The electrosurgical instrument of claim 8, wherein the knife is connected to a knife tube located within an outer tube.

12. The electrosurgical instrument of claim 8, further comprising an outer tube comprising an articulation section coupled to the end effector, the articulation section operatively coupled to first and second articulation bands configured to articulate the end effector.

13. An electrosurgical instrument, comprising:
an end effector comprising a first jaw member and a second jaw member, the first and second jaw members being movable relative to one another from a first, open position to a second, closed position for grasping tissue therebetween;
at least one of the first or second jaw members including a knife channel defined therein configured to reciprocate a knife therealong for severing tissue held between the first and second jaw members;
at least one articulation band including a first articulation band;
an articulation section coupled to the end effector, the articulation section operatively coupled to the at least one articulation band configured to articulate the end effector;
a non-rotatable closure ring; and
a rotatable coupling joint coupled to the articulation section, wherein the rotatable coupling joint comprises:
a rotatable closure ring, wherein a proximal end portion of the rotatable closure ring is coupled to the non-rotatable closure ring; and
a closure link having a distal end portion and a proximal end portion,
wherein the proximal end portion of the closure link is coupled to the rotatable closure ring and the distal end portion of the closure link is coupled to one of the first and second jaw members,
wherein the rotatable closure ring and the closure link are configured to close and open the end effector,
wherein the rotatable closure ring is rotatable relative to the non-rotatable closure ring, which allows the rotatable closure ring to rotate independently of the non-rotatable closure ring while a longitudinal movement of the rotatable closure ring and the non-rotatable closure ring is synchronized,
wherein the rotation of the rotatable closure ring relative to the non-rotatable closure ring results in a rotation of the first and second jaw members, which allows the first and second jaw members to rotate independently of the non-rotatable closure ring.

14. The electrosurgical instrument of claim 13, further comprising at least a second articulation band, wherein the first and second articulation bands are coupled to the rotatable coupling joint.

15. The electrosurgical instrument of claim 13, further comprising a closure tube and a handle assembly operably coupled to the end effector, wherein the first jaw member is movable with respect to the second jaw member, and wherein the first jaw member is coupled to the closure tube and the second jaw member is coupled to the hand assembly.

16. The electrosurgical instrument of claim 14, wherein the at least one articulation band is coupled to the second jaw member through the rotatable coupling joint.

17. An electrosurgical instrument, comprising:
an end effector comprising a first jaw member and a second jaw member, the first and second jaw members being movable relative to one another from a first, open position to a second, closed position for grasping tissue therebetween;
a knife;
at least one of the first and second jaw members including a knife channel defined therein configured to reciprocate the knife therealong for severing tissue held between the first and second jaw members;
an outer tube coupled to the end effector;
a non-rotatable closure ring;
a rotatable coupling joint coupled to the end effector; wherein the rotatable coupling joint comprises:
a rotatable closure ring, wherein a proximal end portion of the rotatable closure ring is coupled to the non-rotatable closure ring; and
a closure link having a distal end portion and a proximal end portion;
a hollow flexible tube coupled to the knife, the hollow flexible tube defining a space therein; and
an active rod that extends longitudinally within the space defined by the hollow flexible tube,
wherein the proximal end portion of the closure link is coupled to the rotatable closure ring and the distal end portion of the closure link is coupled to one of the first and second jaw members,
wherein the rotatable closure ring and the closure link are configured to close and open the end effector,
wherein the rotatable closure ring is rotatable relative to the non-rotatable closure ring, which allows the rotatable closure ring to rotate independently of the non-rotatable closure ring while a longitudinal movement of the rotatable closure ring and the non-rotatable closure ring is synchronized,
wherein the rotation of the rotatable closure ring relative to the non-rotatable closure ring results in a rotation of the first and second jaw members, which allows the first and second jaw members to rotate independently of the non-rotatable closure ring.

18. The electrosurgical instrument of claim 17, wherein the hollow flexible tube is rotatably coupled to the end effector and is configured to rotate the end effector through the knife.

19. The electrosurgical instrument of claim 17, wherein the active rod is configured to electrically couple to one electrical pole of an energy source.

20. The electrosurgical instrument of claim 17, further comprising at least one jaw electrode electrically coupled to at least one of the first or second jaw members, wherein the at least one jaw electrode is adapted to connect to an electrosurgical energy source such that electrosurgical energy may be selectively communicated through tissue held between the first and second jaw members to effect a tissue seal, wherein the at least one jaw electrode defines at least one aperture.

21. The electrosurgical instrument of claim 20, further comprising at least one stop member located on at least one of the first or second jaw members, wherein the stop member is configured to protrude through the at least one aperture of the at least one jaw electrode and to control a gap distance between the first and second jaw members.

* * * * *